(12) United States Patent
Lorincz et al.

(10) Patent No.: US 7,879,546 B2
(45) Date of Patent: *Feb. 1, 2011

(54) ASSESSMENT OF HUMAN PAPILLOMA VIRUS-RELATED DISEASE

(75) Inventors: Attila T. Lorincz, North Potomac, MD (US); James G. Lazar, Bethesda, MD (US)

(73) Assignee: Qiagen Gaithersburg Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/681,539

(22) Filed: Mar. 2, 2007

(65) Prior Publication Data

US 2007/0154884 A1 Jul. 5, 2007

Related U.S. Application Data

(63) Continuation of application No. 09/970,477, filed on Oct. 4, 2001, now Pat. No. 7,291,455, which is a continuation of application No. 09/210,168, filed on Dec. 11, 1998, now Pat. No. 6,355,424.

(60) Provisional application No. 60/082,167, filed on Apr. 17, 1998, provisional application No. 60/070,486, filed on Jan. 5, 1998, provisional application No. 60/069,426, filed on Dec. 12, 1997.

(51) Int. Cl.
*C12Q 1/68* (2006.01)
*C12P 19/34* (2006.01)
*C07H 21/04* (2006.01)

(52) U.S. Cl. .................. 435/6; 435/91.2; 435/91.51; 536/23.72

(58) Field of Classification Search .................. None
See application file for complete search history.

(56) References Cited

U.S. PATENT DOCUMENTS

| | | |
|---|---|---|
| 4,465,078 A | 8/1984 | Manning et al. |
| 4,486,539 A | 12/1984 | Ranki et al. |
| 4,563,417 A | 1/1986 | Albarella et al. |
| 4,563,419 A | 1/1986 | Ranki et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky |
| 4,775,619 A | 10/1988 | Urdea |

(Continued)

FOREIGN PATENT DOCUMENTS

EP 079139 B1 5/1983

(Continued)

OTHER PUBLICATIONS

Bohm, S. et al., *Int'l. J. Cancer*, vol. 55, pp. 791-798, 1993.

(Continued)

*Primary Examiner*—Diana B Johannsen
(74) *Attorney, Agent, or Firm*—Baker Donelson Bearman Caldwell & Berkowitz PC

(57) ABSTRACT

This invention provides methods for assessing HPV infection. Gene expression levels are used to assess the progression of HPV infection from benign to malignant growth. Also provided are kits for carrying out the methods of this invention.

108 Claims, 7 Drawing Sheets

DETECTION OF E6/E7 mRNA FROM CaSki CELLS

U.S. PATENT DOCUMENTS

| | | |
|---|---|---|
| 4,833,084 A | 5/1989 | Carrico |
| 4,851,330 A | 7/1989 | Kohne |
| 4,865,980 A | 9/1989 | Stuart et al. |
| 4,868,105 A | 9/1989 | Urdea et al. |
| 4,889,798 A | 12/1989 | Rabbani |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,256,571 A | 10/1993 | Hurley et al. |
| 5,288,611 A | 2/1994 | Kohne |
| 5,357,977 A | 10/1994 | Michels |
| 5,370,128 A | 12/1994 | Wainwright |
| 5,374,524 A | 12/1994 | Miller |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,527,898 A | 6/1996 | Bauer et al. |
| 5,543,294 A | 8/1996 | Silverstein et al. |
| 5,556,748 A | 9/1996 | Douglas |
| 5,580,970 A | 12/1996 | Hendricks et al. |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,641,630 A | 6/1997 | Snitman et al. |
| 5,656,731 A | 8/1997 | Urdea |
| 5,681,697 A | 10/1997 | Urdea et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,821,339 A | 10/1998 | Schaffer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorinez et al. |
| 5,994,079 A | 11/1999 | De La Rosa et al. |
| 6,027,897 A | 2/2000 | Lorincz et al. |
| 6,043,038 A | 3/2000 | Sivaraja et al. |
| 6,057,099 A | 5/2000 | Nathan et al. |
| 6,083,925 A | 7/2000 | Li et al. |
| 6,110,676 A | 8/2000 | Coull et al. |
| 6,110,682 A | 8/2000 | Dellinger et al. |
| 6,221,581 B1 | 4/2001 | Engelhardt et al. |
| 6,228,578 B1 | 5/2001 | Impraim et al. |
| 6,232,462 B1 | 5/2001 | Collins et al. |
| 6,268,128 B1 | 7/2001 | Collins et al. |
| 6,277,579 B1 | 8/2001 | Lazar et al. |
| 6,326,136 B1 | 12/2001 | Lazar et al. |
| 6,355,424 B1 | 3/2002 | Lorincz et al. |
| 6,436,662 B1 | 8/2002 | Mielzynska et al. |
| 6,521,190 B1 | 2/2003 | Edens et al. |
| 6,544,732 B1 | 4/2003 | Chee et al. |
| 6,583,278 B1 | 6/2003 | Carter |
| 6,686,151 B1 | 2/2004 | Lazar et al. |
| 6,828,098 B2 | 12/2004 | Langmore et al. |
| 6,890,729 B2 | 5/2005 | Mielzynska et al. |
| 6,969,585 B2 | 11/2005 | Lorincz et al. |
| 6,977,148 B2 | 12/2005 | Dean et al. |
| 7,001,776 B2 | 2/2006 | Botacini das Dores et al. |
| 7,291,455 B2 * | 11/2007 | Lorincz et al. ............ 435/6 |
| 7,371,518 B2 | 5/2008 | Lorincz et al. |
| 2001/0055766 A1 | 12/2001 | Aristarkhov et al. |
| 2002/0012936 A1 | 1/2002 | Lorincz et al. |
| 2003/0096232 A1 | 5/2003 | Kris et al. |
| 2003/0108897 A1 | 6/2003 | Drmanac |
| 2003/0175765 A1 | 9/2003 | Kessler et al. |
| 2004/0180362 A1 | 9/2004 | Lazar et al. |
| 2004/0214302 A1 | 10/2004 | Anthony et al. |
| 2005/0147996 A1 | 7/2005 | Sorge |
| 2006/0051809 A1 | 3/2006 | Nazarenko et al. |
| 2006/0160188 A1 | 7/2006 | Kurnit et al. |
| 2008/0200344 A1 | 8/2008 | Cheng |
| 2008/0247914 A1 | 10/2008 | Edens et al. |
| 2009/0032445 A1 | 2/2009 | Doak et al. |
| 2009/0263819 A1 | 10/2009 | Muraca |
| 2009/0298187 A1 | 12/2009 | Nazarenko et al. |
| 2010/0081124 A1 | 4/2010 | Abravaya et al. |

FOREIGN PATENT DOCUMENTS

| | | |
|---|---|---|
| EP | 144914 A2 | 6/1985 |
| EP | 0163220 | 12/1985 |
| EP | 167366 B1 | 1/1986 |
| EP | 184017 A2 | 6/1986 |
| EP | 281297 B1 | 9/1988 |
| EP | 0288737 A1 | 11/1988 |
| EP | 336454 A1 | 10/1989 |
| EP | 0 502 994 B1 | 9/1992 |
| EP | 703296 A1 | 3/1996 |
| WO | 84/02721 | 7/1984 |
| WO | 88/03957 | 6/1988 |
| WO | 89/11546 | 11/1989 |
| WO | 91/08312 A1 | 6/1991 |
| WO | WO 91/08312 | 6/1991 |
| WO | WO 91/08312 A1 | 6/1991 |
| WO | 9310263 | 5/1993 |
| WO | 93/10263 | 6/1993 |
| WO | WO 94/02645 | 2/1994 |
| WO | 94/16108 | 7/1994 |
| WO | 95/16055 | 6/1995 |
| WO | 95/17430 | 6/1995 |
| WO | 9640992 | 5/1996 |
| WO | 96/40992 | 12/1996 |
| WO | 97/05277 | 2/1997 |
| WO | 9705277 | 2/1997 |
| WO | 9710364 | 3/1997 |
| WO | 97/31256 | 8/1997 |
| WO | 98/18488 | 5/1998 |
| WO | 98/22620 | 5/1998 |
| WO | 9818488 | 5/1998 |
| WO | 9822620 | 5/1998 |
| WO | 9859044 | 12/1998 |
| WO | 99/29909 | 6/1999 |
| WO | 99/32654 | 7/1999 |
| WO | 99/36571 | 7/1999 |
| WO | 99/39001 | 8/1999 |
| WO | 99/40224 | 8/1999 |
| WO | 9949224 | 9/1999 |
| WO | 99/50459 | 10/1999 |
| WO | 0060116 | 10/2000 |
| WO | 00/60116 | 11/2000 |
| WO | 0136681 | 5/2001 |
| WO | 0196608 | 12/2001 |
| WO | 2005080602 | 9/2005 |

OTHER PUBLICATIONS

Broker, T.R. et al, *Cancer Cells*, Vo. 7, pp. 197-208, 1989.
DeVilliers et al., "Classification of Papillomaviruses," *Virology*, vol. 324, pp. 17-27, 2004.
Heilman et al., "Cloning of Human Papilloma Virus Genomic DNAs and Analysis of Homologous Polynucleotide Sequence," *Journal of Virology*, vol. 36, No. 2, pp. 395-407, Nov. 1980.

Higgins et al., "Transcription Patterns of Human Papillomavirus Type 16 in Genital Intraepithelial Neoplasia: Evidence for Promoter Usage Within the E7 Open Reading Frame During Epithelial Differentiation," *Journal of General Virology*, vol. 73, pp. 2047-2057, 1992.

Howley et al., "A Rapid Method for Detecting and Mapping Homology between Heterologous DNAs," *The Journal of Biological Chemistry*, vol. 254, No. 11, pp. 4876-4883, Jun. 10, 1979.

H. zur Hauzen, "Papillomavirus Infections-A Major Cause of Human Cancers, *Biochimica et Biophisica Acta*," 1228, pp. F55-F78, Mar. 6, 1996.

Hsu, E.M., et al., "Quantification of HPV-16 E6-E7 Transcription in Cervical Intraepithelial Neoplasia by Reverse Transcriptase Polymerase Chain Reaction," *Int. J. Cancer*, vol. 55, pp. 397-401, Apr. 2, 1993.

Karlsen et al., "Use of Multiple PCR Primer Sets for Optimal Detection of Human Papillomavirus," *Journal of Clinical Microbiology*, pp. 2095-2100, Sep. 1996.

Law et al., "Conserved Polynucleotide Sequence Among the Genomes of Papillomaviruses," *Journal of Virology*, vol. 32, No. 1, pp. 199-207, Oct. 1979.

Lubomir P. Turek, et al., "The Genetic Program of Genital Human Papillomaviruses in Infection and Cancer," *Obstetrics and Gynecology Clinics of North America*, vol. 23, No. 4, pp. 735-758, Dec. 1996.

Lubomir P. Turek, "The Structure, Function, and Regulation of Papillomaviral Genes in Infection and Cervical Cancer," *Advances in Virus Research*, vol. 44, pp. 305-356, 1994.

Mohammed Nasseri, et al., "Human Papillomavirus Type 16 Immortalized Cervical Keratinocytes Contain Transcripts Encoding E6, E7, and E2 Initiated at The P97 Promoter and Express High Levels of E7," *Virology*, vol. 184, pp. 131-140, Feb. 15, 1991.

Nishikawa, A. et al., *Tumor Res.*, No. 31, pp. 73-88 1996.

Park et al., "Physical Status and Expression of HPV Genes in Cervical Cancers," *Gynecologic Oncology*, vol. 65, pp. 121-129, 1997.

Stoler, M.H. et al., "Human Papillomavirus Type 16 and Type 18 Gene Expression in Cervical Neoplasias," *Human Pathology*, vol. 23, No. 2, pp. 117-128, Feb. 1992.

E.M. Hsu et al., "Quantification of HPV-16 E6-E7 Transcription in Cervical Intraepithelial Neoplasia by Reverse Transcriptase Polymerase Chain Reaction," Int. J. Cancer, pp. 397-401, vol. 55, Wiley-Liss, Inc., 1993.

S. Bohm et al., "The Predominant mRNA Class in HPV16-Infected Genital Neoplasias Does Not Encode the E6 or the E7 Protein," Int. J. Cancer, pp. 791-798, vol. 55, Wiley Liss, Inc., 1993.

kate Middleton et al., "Organization of Human Papillomavirus Productive Cycle During Neoplastic Progression Provides a Basis for Selection of Diagnostic Markers," Journal of Virology, pp. 10186-10201, vol. 77, No. 19, American Society for Microbiology, Oct. 2003.

Jong Sup Park, M.D. et al, "Physical Status and Expression of HPV Genes in Cervical Cancers," Gynecologic Oncology, pp. 121-129, vol. 65, art. G0964596, 1997.

Mark H. Stoler et al., "Human Papillomavirus Type 16 and 18 Gene Expression in Cervical Neoplasias," Department of Pathology, The Cleveland Clinic Foundation, pp. 117-128, W.B. Saunders Company, 1992.

Geoffrey D. Higgins et al., "Transcription Patterns of Human Papillomavirus Type 16 in Genital Intraepithelia Neoplasia: Evidence for Promoter Usage within the E7 Open Reading Frame During Epithelial Differentiation," Journal of General Virology, pp. 2047-2057, vol. 73, SGM, 1992.

T.R. Broker et al., "A Molecular Portrait of Human Papillomavirus Carcinogenesis," Cancer Cells 7, Molecular Diagnostics of Human Cancer, pp. 197-208, Cold Spring Harbor Laboratory, 1989.

Frank Karlsen et al., "Use of Multiple PCR Primer Sets for Optimal Detection of Human Papillomavirus," Journal of Clinical Microbiology, pp. 2095-2100, American Society for Microbiology, 1996.

Partial International Search Report for PCT/US2009/062061, mail date Jan. 5, 2010.

Partial International Search Report for PCT/US2009/062041, mail date Jan. 5, 2010.

Bhan P, et al., "2', 5'-linked oligo-3'-deoxyribonucleoside phosphorothioate chimeras: thermal stability and antisense inhibition of gene expression," Nucleic Acids Research Aug. 15, 1997, vol. 25, No. 16, pp. 3310-3317, XP002560367, ISSN: 0305-1048, p. 3313.

Genetech Diagnostics Pvt. Ltd., "Digene HBV Test Hybrid Capture II," Jun. 6, 2008, XP-00256068, retrieved from internet: URL:http://www.gentechin.com/hbvdnatestkit.htm>, the whole document.

Hantz S, et al., "[Evalutation of accuracy of three assays for human papillomavirus detection and typing: Hybrid Capture 2, HPV Consensus kit and Amplicor HPB.]," Pathologie-Biologie, Feb. 2008, vol. 56, No. 1, Feb. 2008, pp. 29-35, XP 002560369, ISSN: 0369-8114, the whole document.

Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146, XP002560370, ISSN: 0095-1137, the whole document.

Boston Bioproducts Inc., "Protein Extraction buffers," Sep. 2, 2007, XP002560371, Retrieved from the Internet: URL: http://www.bostonbioproducts.com/product_disply1.php?page=20&limit=10&id=4>, the whole document.

Bart "General Principles of Immunoprecipitation," Jul. 31, 2008, XP002560372, URL:http://pingu.salk.edu/{sefton/Hyper_protocols/immunoprecip.html>, the whole document.

Thai et al., "An HPV 16, 18, and 45 genotyping test based on Hybrid Capture technology," Journal of Clinical Virology 45, S1 (2009) pp. 593-597.

Kitagawa et al., "Comparison of Poly(A) Poly(dT) and Poly(I) Poly(dC) As Immunogens for the Induction of Antibodies to RNA-DNA Hybrids," Molecular Immunology, vol. 19, No. 3, pp. 413-420, 1982.

Ishikawa et al., "Enzyme-Labeling of Antiboldies and Their Fragments for Enzyme Immunoassay and Immunohistochemical Staining," Journal of Immunoassay and Immunochemistry, 4: 3, 209-327, 1983.

Means et al., "Chemical Modifications of Proteins: History and Applications," Bioconjugate Chem. 1990, 1, 2-12.

Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.

Jakobovits et al., "Germ-line transmission and expression of a human-derived yeast artificial chromosome," pp. 255-258, Nature, vol. 362, Mar. 18, 1993.

U.S. Appl. No. 12/588,304, titled "Automated Assay and System," filed Oct. 9, 2009 (not yet published).

U.S. Appl. No. 12/588,306, titled "Open Platform Automated Sample Processing System," filed Oct. 9, 2009 (not yet published).

U.S. Appl. No. 12/622,131, titled "Multiple-Input Analytical System," filed Nov. 19, 2009 (not yet published).

U.S. Appl. No. 12/605,540, titled "Fast Results Hybrid Capture Assay and System," filed Oct. 26, 2009 (not yet published).

U.S. Appl. No. 12/605,605, titled "Fast Results Hybrid Capture Assay on an Automated Platform," filed Oct. 26, 2009 (not yet published).

International Search Report for PCT/US2009/041033, dated Dec. 22, 2009.

Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.

Michele De Villiers et al., "Classification of papillomarviruses," In: Virology, Jun. 2004, vol. 324(1), pp. 17-27—see table 3.

GenBank Accession No. K02718, "Human papillomavirus type 16 (HPV16), complete genome.", Mar. 18, 1994. See http://www.ncbi.nlm.nihgov/nuccore/333031.

GenBank Accession No. X74479, "human papillomavirus type 45 genomic DNA.", Apr. 18, 2005. See http://www.ncbi.nlm.nih.gov/nuccore/397022.

GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.

GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi_nlm.nih.gov/nuccore/397038.
GenBank Accession No. X74483, "Human papillomavirus type 56 genomic DNA.", Apr. 18, 2005. See http://www.ncbi_nlm.nih.gov/nuccore/397053.
GenBank Accession No. D90400, "Human papillomavirus type 58, complete genome.", Dec. 7, 2007. See http://www.ncbi.nlm_nih.govinuccore/222386.
GenBank Accession No. X77858, "Human papillomavirus type 59, complete viral genome.", Apr. 18, 2005. See http://www.ncbi.nlm_nih.gov/nuccore/557236.
GenBank Accession No. U31794, "Human papillomavirus type 66, complete genome.", Oct. 18, 1995. See http://www.ncbi.nlm_nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.
GenBank Accession No. AB027021, "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
Lowe, et al., "A computer program for selection of oligonucleotide primers for polymerase chain reactions", Nucleic Acid Res., vol. 18, No. 7, pp. 1757-1761 (1990).
Chandler et al. Detection of dengue-2 viral RNA by reversibletarget capture hybridization. J Clin Microbiol., vol. 31 (10), pp. 2641-2647, 1993.
Murakami et al. Fluorescent-labeled oligonucleotide probes: detection of hybrid formation in solution by fluorscence polarization spectroscopy. Nucleic Acids Res., vol. 19, Np. 15, pp. 4097-4102, 1991.
Mazzulli et al. Multicenter comparison of the Digene hybrid capture CMV DNA assay (version 2.0), the pp65 antignenemia assay, and cell culture for detection of cytomegalovirus viremia. J. Clin. Microbiol., vol. 37, No. 4, pp. 958-963, 1999.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR-Based Method for the Detection of Mycobacterium genavense" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acids Research, 26:5581-5588, 1998.
Gelmetti et al., "Detection of Rabbit Haemorrhagic Disease Virus (RHDV) by in Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of Salmonella by Using the Colorimetric DNA/rRNA Sandwich Hybridization in Microtiter Wells" J. Vet. Med. Sci. 62:615-619, 2000.
Lazar et al., 1999 "Hybrid Capture.RTM.: a Sensitive Signal Amplification-based Chemiluminescent Test for the Detection and Quantitation of Human Viral and Bacterial Pathogens" J. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" J. Biol. Chem. 265:11601-11604.
Stollar, B.D. and A. Rashtchian, 1987 "Immunochemical Approaches to Gene Probe Assays" Anal. Biochem. 161;387-394.
Blais, B.W., 1994 "Transcriptional Enhancement of the Listeria Monocytogenes PCR and Simple Immunoenzymatic Assay of the Product Using Anti-RNA:DNA Antibodies" Appl. Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Marker 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of Helicobacter pylori PCR Products from Biopsy Specimens Journal of Clinical Microbiology, 35:2931-2936.
Chiu et al., 1998 "Sandwich-type Deoxyribonucleic Acid Hybridization Assays Based on Enzyme Amplified Time-Resolved Fluorometry" Analyst., 123:1315-1319.
White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.

Zammatteo et al., 1997 "Comparison between Microwell and Bead Supports for the Detection of Human Cytomegalovirus Amplicons by Sandwich Hybridization" Analytical Biochemistry 253:180-189.

Fisher et al., 1997 "A System for the Quantitation of DNA Using a Microtiter Plate-Based Hybridization and Enzyme Amplification Technology" Analytical Biochemistry 251:280-287.

Wicks et al., 1998 "A Sandwich Hybridization Assay Employing Enzyme Amplification for Determination of Specific Ribosomal RNA from Unpurified Cell Lysates" Analytical Biochemistry 259:258-264.

Bruckner-Lea et al., 2000 "Rotating Rod Renewable Microcolumns for Automated, Solid-Phase DNA Hybridization Studies" Anal. Chem. 72:4135-4141.

Allen et al., 1998 "High Resolution Genetic Typing of the Class II HLA-DRB1 Locus Using Group-Specific Amplification and SSO-Hybridisation in Microplates" Hereditas 129:161-167.

Chomvarin et al., 2000 "Development of EIA for Detection of Chlamydia trachomatis in Genital Specimens" The Southeast Asian Journal of Tropical Medicine and Public Health, 31:96-103.

Alexandre et al., 1998 "Quantitative Determination of CMV DNA Using a Combination of Competitive PCR Amplification and Sandwich Hybridization" BioTechniques, 25: 676-683.

Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.

Communication received from the European Patent Office pursuant to Application No. 01 944 578.2-2402, Jun. 29, 2006.

Dunn and Hassell: "A Novel Method to Map Transcripts: Evidence for Homology between an Adenovirus mRNA and Discrete Multiple Regions of the Viral Genome" Cell, 12:23-36, Sep. 1977.

International Search Report PCT/US06160603 mailed Sep. 11, 2007.

McGeoch et al. "Structures of Herpes Simplex Virus Type 1 Genes Required for Replication of Virus DNA" J. Virol. vol. 62, No. 2, pp. 444-453, Feb. 1998.

Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.

Lorincz, A.T., "Molecular Methods for the Detection of Human Papillomavirus Infection", Obstetrics and Gynecology Clinics of North America, vol. 23, No. 3, pp. 707-730, Sep. 1996.

Larder et al. "Related functional domains in virus DNA polymerases", The EMBO J., 1987, vol. 6, No. 1, pp. 169-175.

McGeoch et al. "The Complete DNA Sequence of the Long Unique Region in the Genome of Herpes Simplex Virus Type I", J. Gen. Virol., 1998, vol. 69, pp. 1531-1574.

Yamada et al "Human Papillomavirus Type 16 Variant Lineages in United States Populations Characterized by Nucleotide Sequence Analysis of the E6, L2, and L1 Coding Segments", J.Virol. Dec. 1995, vol. 69, No. 12, pp. 7743-7753.

Hara et al. "Small Sample Whole-Genome Amplification", Optics East 2005, UCRL-PROC-216415, Lawrence Livermore National Laboratory, Oct. 21, 2005.

Brigotti, et al. Nucleic Acids Res., vol. 26, No. 18, pp. 4306-4307, 1998.

EPO Form 1507.4 (Supplementary European Search Report)., Aug. 2004.

Goldsborough et al., "Nucleotide sequence of human papillomavirus type 31: A cervical neoplasia-associated virus," Virology, 171:306-311,1989.

Swain M.A. et al., "Nucleotide sequence of the herpes simplex virus type 2 thymidine kinase gene," J. Virol., 46 (3):1045-1050, especially p. 1047, Jun. 1983.

Delius, H. et al., "Primer-directed sequencing of human papillomavirus types," Curr. Top. Microbiol. Immunol., 186:13-31, especially p. 16, 1994.

McGeoch et al. DNA Sequence and Genetic Content of the HindIII 1 Region in the Short Unique Component of the Herpes Simplex Virus Type 2 Genomel Identification of the Gene Encoding Glycoprotein G, and Evolutionary Comparisons J. Gen. Virol. 1987, vol. 68, pp. 19-38.

Dalrymple et al. "DNA Sequence of the herpes simplex virus type 1 gene whose product is responsible for transcriptional activation of immediate early promoters", Nucleic Acids Research, 1985, vol. 13, No. 21, pp. 7865-7879.

McLauchlan et al., "DNA sequence homology between two co-linear loci on the HSV genome which have different transforming abilities" The EMBO Journal, 1983, vol. 2, No. 11, pp. 1953-1961.

Blair et al., "Herpes Simplex Virus Viron Stimulatory Protein mRNA Leader Contains Sequence Elements Which Increase Both Virus-Induced Transcription and mRNA Stability", Journal of Virology, vol. 61, No. 8, pp. 2499-2508, Aug. 1987.

Lowe et al., "Assessing HPV-related disease through detection of HPV mRNA rations", Poster, Qiagen Inc., Gaithersburg, MD, 2009.

International Search Report and Written Opinion of PCT/US2010/022264 dated Jun. 7, 2010 (19 pages).

Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.

Gentech Diagnostics: "Chlamydia DNA Test Kit," (Jun. 6, 2008), XP002578832, Retrieved from the Internet: URL:http://www.gentechin.com/chlamydiatestkit.htm.

Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.

Darwin et al., "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.

Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.

Mittendorf T, et al., "HPV-DNA-Diagnostik zur Zervixkarzinomfrüherkennung; Deutsche Agentur für HTA des Deutschen Instituts für Medizinische Dokumentation und Information," 1. Auflage 2007, (portions in English language considered).

Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.

Davey DD, et al., "Introduction and Commentary, Strategic Science Symposium, Human Papillomavirus Testing—Are you ready for a new era in cervical cancer screening?," Arch Pathol Lab Med, 127:927-929, Aug. 2003.

Malloy C, et al., "HPV DNA Testing: Technical and Programmatic Issues for Cervical Cancer Prevention in Low-Resource Settings," Path, Dec. 2000.

Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.

Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).

Bohm S, et al., "The Predominant mRNA Class in HPV16-Infected Genital Neoplasias does not Encode the E6 or the E7 Protein," Int J. Cancer: 55, 791-798 (1993).

Middleton, K, et al., "Organization of Human Papillomavirus Productive Cycle during Neoplastic Progression Provides a Basis for Selection of Diagnostic markers," Journal of Virology, Oct. 2003, pp. 10186-10201.

Stoler, M, et al., "Human Papillomavirus Type 16 and 18 Gene Expression in Cervical Neoplasias," Human Pathol. 23 (1992), pp. 117-128.

Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.

Karlsen, F, et al., "Use of Multiple PCR Primer Sets for Optimal Detection of Human Papillomavirus," J. Clin. Microbiol. 34 (1996), pp. 2095-2100.
Park, JS, et al., "Physical Status and Expression of HPV Genes in Cervical Cancers," Gynec. Oncol. 95 (1997), pp. 121-129.
Broker, TR, et al., "A Molecular Portrait of Human Papillomavirus Carcinogenesis," Cancer Cells 7 (1989), pp. 197-207.
Letter dated Jan. 6, 2010 to EPO re EP 1 038 022 (46 pages).
Letter to EPO dated Mar. 2, 2009 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
International Search Report for PCT/US2009/062041, Patent Cooperation Treaty, Mar. 31, 2010 (17 pages).
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6.
Vernick et al., "The HPV DNA virus hybrid capture assay: What is it- and where do we go from here?" MLO Med. Lab. Obs., (Mar. 2003), pp. 8-10, 13, vol. 35, No. 3.
Supplementary European Search Report of PCT/US2006/060603, dated Jul. 7, 2010 (8 pages).

* cited by examiner

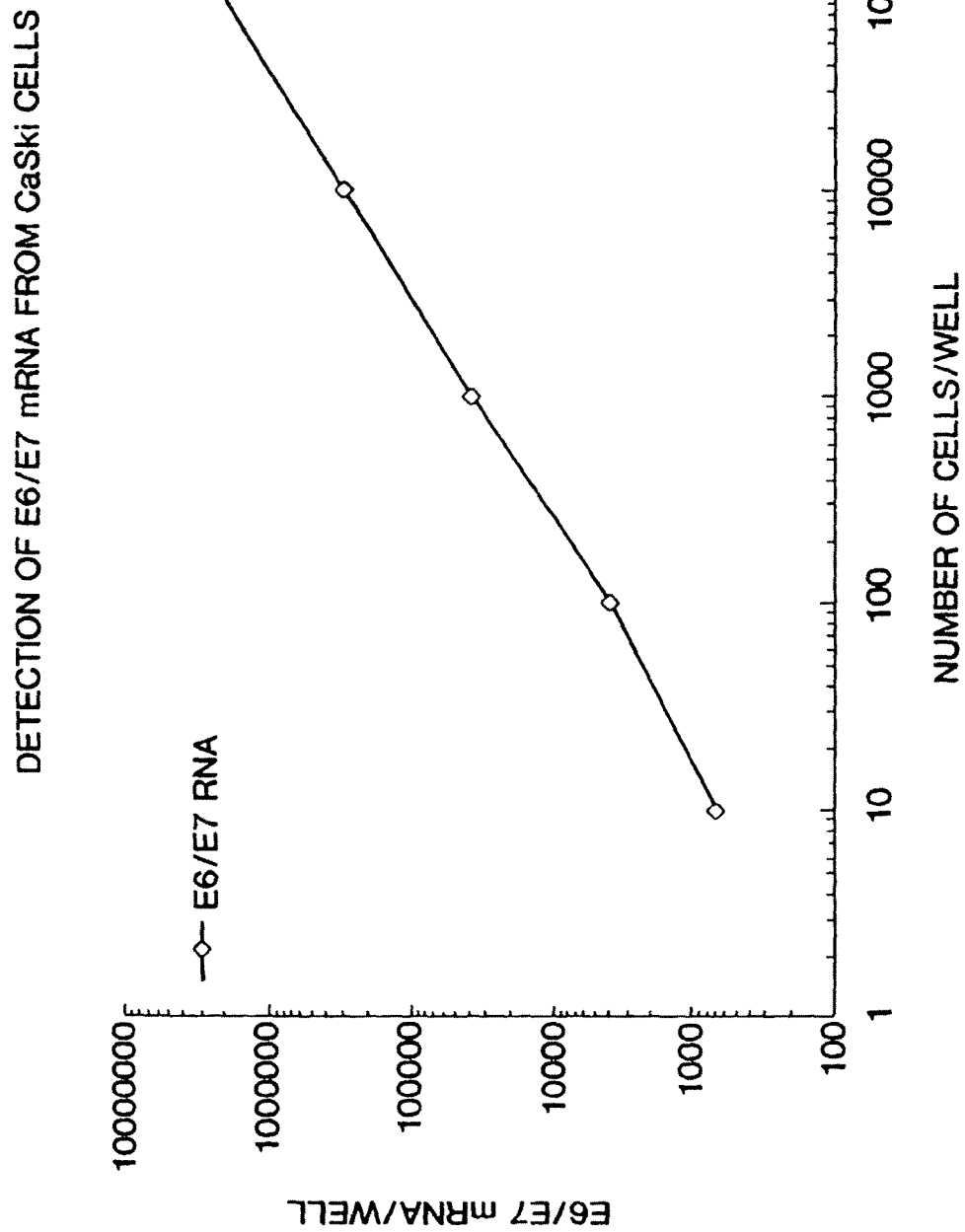

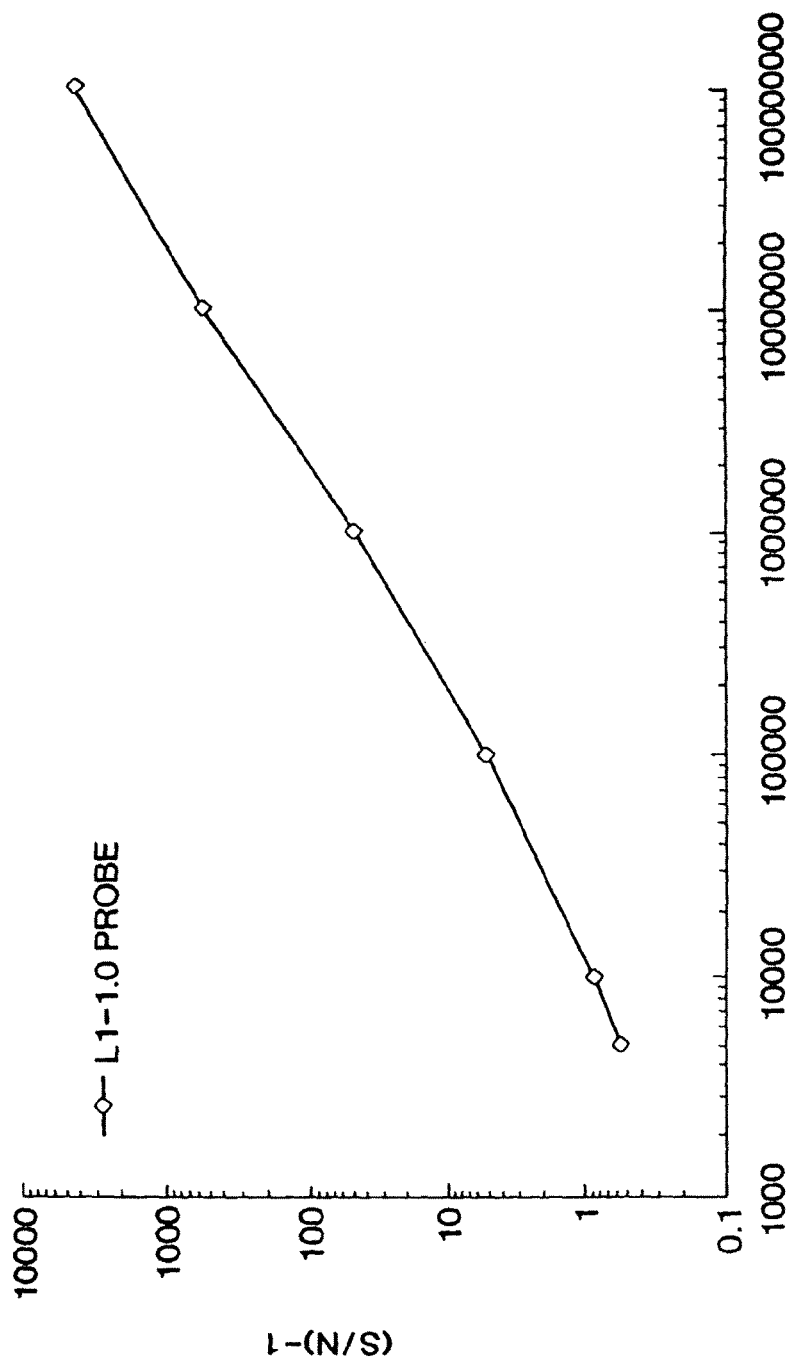

L2-HPV16

TTGTTGTATACCATAACTTACTATTTTTTCTTTTTTATTTTCATATATAATTTTTTTTTT
TGTTTGTTTGTTTGTTTTTTAATAAACTGTTATTACTTAACAATGCGACACAAACGTTCT
GCAAAACGCACAAAACGTGCATCGGCTACCCAACTTTATAAAACATGCAAACAGGCAGGT
ACATGTCCACCTGACATTATACCTAAGGTTGAAGGCAAAACTATTGCTGAACAAATATTA
CAATATGGAAGTATGGGTGTATTTTTTGGTGGGTTAGGAATTGGAACAGGGTCGGGTACA
GGCGGACGCACTGGGTATATTCCATTGGGAACAAGGCCTCCCACAGCTACAGATACACTT
GCTCCTGTAAGACCCCCTTTAACAGTAGATCCTGTGGGCCCTTCTGATCCTTCTATAGTT
TCTTTAGTGGAAGAAACTAGTTTTATTGATGCTGGTGCACCAACATCTGTACCTTCCATT
CCCCCAGATGTATCAGGATTTAGTATTACTACTTCAACTGATACCACACCTGCTATATTA
GATATTAATAATACTGTTACTACTGTTACTACACATAATAATCCCACTTTCACTGACCCA
TCTGTATTGCAGCCTCCAACACCTGCAGAAACTGGAGGGCATTTTACACTTTCATCATCC
ACTATTAGTACACATAATTATGAAGAAATTCCTATGGATACATTTATTGTTAGCACAAAC
CCTAACACAGTAACTAGTAGCACACCCATACCAGGGTCTCGCCCAGTGGCACGCCTAGGA
TTATATAGTCGCACAACACAACAGGTTAAAGTTGTAGACCCTGCTTTTGTAACCACTCCC
ACTAAACTTATTACATATGATAATCCTGCATATGAAGGTATAGATGTGGATAATACATTA
TATTTTTCTAGTAATGATAATAGTATTAATATAGCTCCAGATCCTGACTTTTTGGATATA
GTTGCTTTACATAGGCCAGCATTAACCTCTAGGCGTACTGGCATTAGGTACAGTAGAATT
GGTAATAAACAAACACTACGTACTCGTAGTGGAAAATCTATAGGTGCTAAGGTACATTAT
TATTATGATTTAAGTACTATTGATCCTGCAGAAGAAATAGAATTACAAACTATAACACCT
TCTACATATACTACCACTTCACATGCAGCCTCACCTACTTCTATTAATAATGGATTATAT
GATATTTATGCAGATGACTTTATTACAGATACTTCTACAACCCCGGTACCATCTGTACCC
TCTACATCTTTATCAGGTTATATTCCTGCAAATACAACAATTCCTTTTGGTGGTGCATAC
AATATTCCTTTAGTATCAGGTCCTGATATACCCATTAATATAACTGACCAAGCTCCTTCA
TTAATTCCTA

Fig. 3

L1-HPV16

GAGGCCACTGTCTACTTGCCTCCTGTCCCAGTATCTAAGGTTGTAAGCACGGATGAATAT
GTTGCACGCACAAACATATATTATCATGCAGGAACATCCAGACTACTTGCAGTTGGACAT
CCCTATTTTCCTATTAAAAAACCTAACAATAACAAAATATTAGTTCCTAAAGTATCAGGA
TTACAATACAGGGTATTTAGAATACATTTACCTGACCCCAATAAGTTTGGTTTTCCTGAC
ACCTCATTTTATAATCCAGATACACAGCGGCTGGTTTGGGCCTGTGTAGGTGTTGAGGTA
GGTCGTGGTCAGCCATTAGGTGTGGGCATTAGTGGCCATCCTTTATTAAATAAATTGGAT
GACACAGAAAATGCTAGTGCTTATGCAGCAAATGCAGGTGTGGATAATAGAGAATGTATA
TCTATGGATTACAAACAAACACAATTGTGTTTAATTGGTTGCAAACCACCTATAGGGGAA
CACTGGGGCAAAGGATCCCCATGTACCAATGTTGCAGTAAATCCAGGTGATTGTCCACCA
TTAGAGTTAATAAACACAGTTATTCAGGATGGTGATATGGTTCATACTGGCTTTGGTGCT
ATGGACTTTACTACATTACAGGCTAACAAAAGTGAAGTTCCACTGGATATTTGTACATCT
ATTTGCAAATATCCAGATTATATTAAAATGGTGTCAGAACCATATGGCGACAGCTTATTT
TTTTATTTACGAAGGGAACAAATGTTTGTTAGACATTTATTTAATAGGGCTGGTACTGTT
GGTGAAAATGTACCAGACGATTTATACATTAAAGGCTCTGGGTCTACTGCAAATTTAGCC
AGTTCAAATTATTTTCCTACACCTAGTGGTTCTATGGTTACCTCTGATGCCCAAATATTC
AATAAACCTTATTGGTTACAACGAGCACAGGGCCACAATAATGGCATTTGTTGGGGTAAC
CAACTATTTGTTACTGTTGTTGATACTACACGCAGTACAAATATGTCATTATGTGCTGCC
ATATCTACTTCAGAAACTACATATAAAAATACTAACTTTAAGGAGTACCTACGACATGGG
GAGGAATATGATTTACAGTTTATTTTTCAACTGTGCAAAATAACCTTAACTGCAGACGTT
ATGACATACATACATTCTATGAATTCCACTATTTTGGAGGACTGGAATTTTGGTCTACAA
CCTCCCCCAGGAGGCACACTAGAAGATACTTATAGGTTTGTAACCCAGGCAATTGCTTGT
CAAAAACATACACCTCCAGCACCTAAGAAGATGATCCCCTTAAAAAATACACTTTTTGG
GAAGTAAATTTAAAGGAAAAGTTTTCTGCAGACCTAGATCAGTTTCCTTTAGGACGCAAA
TTTTTACTACAAGCAGGATTGAAGGCCAAACCAAAATTTACATTAGGAAAACGAAAAGCT
ACACCCACCACCTCATCTACCTCTACAACTGCTAAACGCAAAAA

Fig. 4

E6/E7-HPV16

ACATTTTATGCACCAAAAGAGAACTGCAATGTTTCAGGACCCACAGGAGCGACCCAGAAA

GTTACCACAGTTATGCACAGAGCTGCAAACAACTATACATGATATAATATTAGAATGTGT

GTACTGCAAGCAACAGTTACTGCGACGTGAGGTATATGACTTTGCTTTTCGGGATTTATG

CATAGTATATAGAGATGGGAATCCATATGCTGTATGTGATAAATGTTTAAAGTTTTATTC

TAAAATTAGTGAGTATAGACATTATTGTTATAGTTTGTATGGAACAACATTAGAACAGCA

ATACAACAAACCGTTGTGTGATTTGTTAATTAGGTGTATTAACTGTCAAAAGCCACTGTG

TCCTGAAGAAAAGCAAAGACATCTGGACAAAAAGCAAAGATTCCATAATATAAGGGGTCG

GTGGACCGGTCGATGTATGTCTTGTTGCAGATCATCAAGAACACGTAGAGAAACCCAGCT

GTAATCATGCATGGAGATACACCTACATTGCATGAATATATGTTAGATTTGCAACCAGAG

ACAACTGATCTCTACTGTTATGAGCAATTAAATGACAGCTCAGAGGAGGAGGATGAAATA

GATGGTCCAGCTGGACAAGCAGAACCGGACAGAGCCCATTACAATATTGTAACCTTTTGT

TGCAAGTGTGACTCTACGCTTCGGTTGTGCGTACAAAGCACACACGTAGACATTCGTACT

TTGGAAGACCTGTTAATGGGCACACTAGGAATTGTGTGCCCCATCTGTTCTCAGAAACC

Fig. 5

E-2 HPV16

GAGGACGAGGACAAGGAAAACGATGGAGACTCTTTGCCAACGTTTAAATGTGTGTCAGGA

CAAAATACTAACACATTATGAAAATGATAGTACAGACCTACGTGACCATATAGACTATTG

GAAACACATGCGCCTAGAATGTGCTATTTATTACAAGGCCAGAGAAATGGGATTTAAACA

TATTAACCACCAAGTGGTGCCAACACTGGCTGTATCAAAGAATAAAGCATTACAAGCAAT

TGAACTGCAACTAACGTTAGAAACAATATATAACTCACAATATAGTAATGAAAAGTGGAC

ATTACAAGACGTTAGCCTTGAAGTGTATTTAACTGCACCAACAGGATGTATAAAAAAACA

TGGATATACAGTGGAAGTGCAGTTTGATGGAGACATATGCAATACAATGCATTATACAAA

CTGGACACATATATATTTGTGAAGAAGCATCAGTAACTGTGGTAGAGGGTCAAGTTGA

CTATTATGGTTTATATTATGTTCATGAAGGAATACGAACATATTTTGTGCAGTTTAAAGA

TGATGCAGAAAAATATAGTAAAAATAAAGTATGGGAAGTTCATGCGGGTGGTCAGGTAAT

ATTATGTCCTACATCTGTGTTTAGCAGCAACGAAGTATCCTCTCCTGAAATTATTAGGCA

GCACTTGGCCAACCACCCCGCCGCGACCCATACCAAAGCCGTCGCCTTGGGCACCGAAGA

AACACAGACGACTATCCAGCGACCAAGATCAGAGCCAGACACCGGAAACCCCTGCCACAC

CACTAAGTTGTTGCACAGAGACTCAGTGGACAGTGCTCCAATCCTCACTGCATTTAACAG

CTCACACAAAGGACGGATTAACTGTAATAGTAACACTACACCCATAGTACATTTAAAAGG

TGATGCTAATACTTTAAAATGTTTAAGATATAGATTTAAAAAGCATTGTACATTGTATAC

TGCAGTGTCGTCTACATGGCATTGGACAGGACATAATGTAAAACATAAAAGTGCAATTGT

TACACTTACATATGATAGTGAATGGCAACGTGACCAATTTTTGTCTCAAGTTAAAATACC

AAAAACTATTACAGTGTCTACTGGATTTATGTC

Fig. 6

E4-HPV16

CTACATCTGTGTTTAGCAGCAACGAAGTATCCTCTCCTGAAATTATTAGGCAGCACTTGG

CCAACCACCCCGCCGCGACCCATACCAAAGCCGTCGCCTTGGGCACCGAAGAAACACAGA

CGACTATCCAGCGACCAAGATCAGAGCCAGACACCGGAAACCCCTGCCACACCACTAAGT

TGTTGCACAGAGACTCAGTGGACAGTGCTCCAATCCTCACTGCATTTAACAGCTCACACA

AAGGACGGATTAACTGTAATAG

Fig. 7

SEQUENCE LISTING

```
<160> NUMBER OF SEQ ID NOS: 5

<210> SEQ ID NO 1
<211> LENGTH: 1390
<212> TYPE: DNA
<213> ORGANISM: Human papillomavirus
<220> FEATURE:
<223> OTHER INFORMATION: L2-HPV16

<400> SEQUENCE: 1
ttgttgtata ccataactta ctatttttc tttttatt tcatatataa tttttttttt      60
tgtttgtttg tttgttttt aataaactgt tattacttaa caatgcgaca caaacgttct    120
gcaaaacgca caaacgtgc atcggctacc caactttata aaacatgcaa acaggcaggt    180
acatgtccac ctgacattat acctaaggtt gaaggcaaaa ctattgctga acaaatatta    240
caatatggaa gtatgggtgt attttttggt gggttaggaa ttggaacagg gtcgggtaca    300
ggcggacgca ctgggtatat tccattggga acaaggcctc ccacagctac agatacactt    360
gctcctgtaa gaccccttt aacagtagat cctgtgggcc cttctgatcc ttctatagtt    420
tctttagtgg aagaaactag ttttattgat gctggtgcac caacatctgt accttccatt    480
cccccagatg tatcaggatt tagtattact acttcaactg ataccacacc tgctatatta    540
gatattaata atactgttac tactgttact acacataata atcccacttt cactgaccca    600
```

| | |
|---|---:|
| tctgtattgc agcctccaac acctgcagaa actggagggc attttacact ttcatcatcc | 660 |
| actattagta cacataatta tgaagaaatt cctatggata catttattgt tagcacaaac | 720 |
| cctaacacag taactagtag cacacccata ccagggtctc gcccagtggc acgcctagga | 780 |
| ttatatagtc gcacaacaca acaggttaaa gttgtagacc ctgcttttgt aaccactccc | 840 |
| actaaactta ttacatatga taatcctgca tatgaaggta tagatgtgga taatacatta | 900 |
| tattttccta gtaatgataa tagtattaat atagctccag atcctgactt tttggatata | 960 |
| gttgctttac ataggccagc attaacctct aggcgtactg gcattaggta cagtagaatt | 1020 |
| ggtaataaaac aaacactacg tactcgtagt ggaaaatcta taggtgctaa ggtacattat | 1080 |
| tattatgatt taagtactat tgatcctgca gaagaaatag aattacaaac tataacacct | 1140 |
| tctacatata ctaccacttc acatgcagcc tcacctactt ctattaataa tggattatat | 1200 |
| gatatttatg cagatgactt tattacagat acttctacaa ccccggtacc atctgtaccc | 1260 |
| tctacatctt tatcaggtta tattcctgca aatacaacaa ttccttttgg tggtgcatac | 1320 |
| aatattcctt tagtatcagg tcctgatata cccattaata taactgacca agctccttca | 1380 |
| ttaattccta | 1390 |

<210> SEQ ID NO 2
<211> LENGTH: 1484
<212> TYPE: DNA
<213> ORGANISM: Human papillomavirus
<220> FEATURE:
<223> OTHER INFORMATION: L1-HPV16

<400> SEQUENCE: 2

| | |
|---|---:|
| gaggccactg tctacttgcc tcctgtccca gtatctaagg ttgtaagcac ggatgaatat | 60 |
| gttgcacgca caaacatata ttatcatgca ggaacatcca gactacttgc agttggacat | 120 |
| ccctattttc ctattaaaaa acctaacaat aacaaaatat tagttcctaa agtatcagga | 180 |
| ttacaataca gggtatttag aatacatttta cctgacccca taagtttggg ttttcctgac | 240 |
| acctcatttt ataatccaga tacacagcgg ctggtttggg cctgtgtagg tgttgaggta | 300 |
| ggtcgtggtc agccattagg tgtgggcatt agtggccatc ctttattaaa taaattggat | 360 |
| gacacagaaa atgctagtgc ttatgcagca aatgcaggtg tggataatag agaatgtata | 420 |
| tctatggatt acaaacaaac acaattgtgt ttaattggtt gcaaaccacc tataggggaa | 480 |
| cactggggca aaggatcccc atgtaccaat gttgcagtaa atccaggtga ttgtccacca | 540 |
| ttagagttaa taaacacagt tattcaggat ggtgatatgg ttcatactgg ctttggtgct | 600 |
| atggactttta ctacattaca ggctaacaaa agtgaagttc cactggatat ttgtacatct | 660 |
| atttgcaaat atccagatta tattaaaatg gtgtcagaac catatggcga cagcttattt | 720 |
| ttttatttac gaagggaaca aatgtttgtt agacatttat ttaatagggc tggtactgtt | 780 |
| ggtgaaaatg taccagacga tttatacatt aaaggctctg gtctactgc aaatttagcc | 840 |
| agttcaaatt atttttccta cctagtggt tctatggtta cctctgatgc ccaaatattc | 900 |
| aataaaccctt attggttaca acgagcacag ggccacaata tggcatttgt tggggtaac | 960 |
| caactatttg ttactgttgt tgatactaca cgcagtacaa atatgtcatt atgtgctgcc | 1020 |
| atatctactt cagaaactac atataaaaat actaacttta aggagtacct acgacatggg | 1080 |
| gaggaatatg atttacagtt tattttttcaa ctgtgcaaaa taaccttaac tgcagacgtt | 1140 |
| atgcataca tacattctat gaattccact attttggagg actggaattt tggtctacaa | 1200 |
| cctccccccag gaggcacact agaagatact tataggtttg taacccaggc aattgcttgt | 1260 |

| | |
|---|---:|
| caaaaacata cacctccagc acctaaagaa gatgatcccc ttaaaaaata cactttttgg | 1320 |
| gaagtaaatt taaaggaaaa gttttctgca gacctagatc agtttccttt aggacgcaaa | 1380 |
| tttttactac aagcaggatt gaaggccaaa ccaaaattta cattaggaaa acgaaaagct | 1440 |
| acacccacca cctcatctac ctctacaact gctaaacgca aaaa | 1484 |

```
<210> SEQ ID NO 3
<211> LENGTH: 779
<212> TYPE: DNA
<213> ORGANISM: Human papillomavirus
<220> FEATURE:
<223> OTHER INFORMATION: E6/E7-HPV16

<400> SEQUENCE: 3
```

| | |
|---|---:|
| acattttatg caccaaaaga gaactgcaat gtttcaggac ccacaggagc gacccagaaa | 60 |
| gttaccacag ttatgcacag agctgcaaac aactatacat gatataatat tagaatgtgt | 120 |
| gtactgcaag caacagttac tgcgacgtga ggtatatgac tttgcttttc gggatttatg | 180 |
| catagtatat agagatggga atccatatgc tgtatgtgat aaatgtttaa agttttattc | 240 |
| taaaattagt gagtatagac attattgtta gtttgtat ggaacaacat tagaacagca | 300 |
| atacaacaaa ccgttgtgtg atttgttaat taggtgtatt aactgtcaaa agccactgtg | 360 |
| tcctgaagaa aagcaaagac atctggacaa aaagcaaaga ttccataata taaggggtcg | 420 |
| gtggaccggt cgatgtatgt cttgttgcag atcatcaaga acacgtagag aaacccagct | 480 |
| gtaatcatgc atggagatac acctacattg catgaatata tgttagattt gcaaccagag | 540 |
| acaactgatc tctactgtta tgagcaatta aatgacagct cagaggagga ggatgaaata | 600 |
| gatggtccag ctggacaagc agaaccggac agagcccatt acaatattgt aaccttttgt | 660 |
| tgcaagtgtg actctacgct tcggttgtgc gtacaaagca cacgtagac attcgtact | 720 |
| ttggaagacc tgttaatggg cacactagga attgtgtgcc ccatctgttc tcagaaacc | 779 |

```
<210> SEQ ID NO 4
<211> LENGTH: 1113
<212> TYPE: DNA
<213> ORGANISM: Human papillomavirus
<220> FEATURE:
<223> OTHER INFORMATION: E2- HPV16

<400> SEQUENCE: 4
```

| | |
|---|---:|
| gaggacgagg acaaggaaaa cgatggagac tctttgccaa cgtttaaatg tgtgtcagga | 60 |
| caaaatacta acacattatg aaaatgatag tacagaccta cgtgaccata tagactattg | 120 |
| gaaacacatg cgcctagaat gtgctattta ttacaaggcc agagaaatgg gatttaaaca | 180 |
| tattaaccac caagtggtgc caacactggc tgtatcaaag aataaagcat tacaagcaat | 240 |
| tgaactgcaa ctaacgttag aaacaatata taactcacaa tatagtaatg aaaagtggac | 300 |
| attacaagac gttagccttg aagtgtattt aactgcacca caggatgta taaaaaaaca | 360 |
| tggatataca gtggaagtgc agtttgatgg agacatatgc aatacaatgc attatacaaa | 420 |
| ctggacacat atatatattt gtgaagaagc atcagtaact gtggtagagg gtcaagttga | 480 |
| ctattatggt ttatattatg ttcatgaagg aatacgaaca tattttgtgc agtttaaaga | 540 |
| tgatgcagaa aaatatagta aaaataaagt atgggaagtt catgcgggtg gtcaggtaat | 600 |
| attatgtcct acatctgtgt ttagcagcaa cgaagtatcc tctcctgaaa ttattaggca | 660 |
| gcacttggcc aaccacccg ccgcgaccca taccaaagcc gtcgccttgg gcaccgaaga | 720 |

```
-continued aacacagacg actatccagc gaccaagatc agagccagac accggaaacc cctgccacac      780
cactaagttg ttgcacagag actcagtgga cagtgctcca atcctcactg catttaacag      840
ctcacacaaa ggacggatta actgtaatag taacactaca cccatagtac atttaaaagg      900
tgatgctaat actttaaaat gtttaagata tagatttaaa aagcattgta cattgtatac      960
tgcagtgtcg tctacatggc attggacagg acataatgta aaacataaaa gtgcaattgt     1020
tacacttaca tatgatagtg aatggcaacg tgaccaatt ttgtctcaag ttaaaatacc      1080
aaaaactatt acagtgtcta ctggatttat gtc                                  1113

<210> SEQ ID NO 5
<211> LENGTH: 262
<212> TYPE: DNA
<213> ORGANISM: Human papillomavirus
<220> FEATURE:
<223> OTHER INFORMATION: E4-HPV16

<400> SEQUENCE: 5
ctacatctgt gtttagcagc aacgaagtat cctctcctga aattattagg cagcacttgg       60
ccaaccaccc cgccgcgacc cataccaaag ccgtcgcctt gggcaccgaa gaaacacaga      120
cgactatcca gcgaccaaga tcagagccag acaccggaaa ccctgccac accactaagt       180 tgttgcacag agactcagtg gacagtgctc caatcctcac tgcatttaac agctcacaca      240
aaggacggat taactgtaat ag                                               262
```

ASSESSMENT OF HUMAN PAPILLOMA VIRUS-RELATED DISEASE

This application is a continuation application of U.S. patent application Ser. No. 09/970,477, filed Oct. 4, 2001, issued as U.S. Pat. No. 7,291,455 on Nov. 6, 2007, which is a continuation of Ser. No. 09/210,168, filed Dec. 11, 1998, issued as U.S. Pat. No. 6,355,424 on Feb. 21, 2002, to which priority under 35 U.S.C. §120 is claimed. This application also claims benefit of U.S. Patent Application Ser. Nos. 60/082,167, filed Apr. 17, 1998, 60/070,486, filed Jan. 5, 1998, and 60/069,426, filed Dec. 12, 1997.

FIELD OF THE INVENTION

The present invention is generally related to the field of cytological and molecular assays and specifically to the area of assays for the assessment of disease using a sensitive assay for diagnosis and prognosis of HPV-induced carcinoma.

BACKGROUND OF THE INVENTION

The detection and diagnosis of disease is of obvious importance for the treatment of disease. Numerous characteristics of diseases have been identified and many are used for the diagnosis of disease. Many diseases are preceded by, and are characterized by, changes in the state of the affected cells. Changes can include the expression of viral genes in infected cells, changes in the expression patterns of genes in affected cells, and changes in cell morphology. The detection, diagnosis, and monitoring of diseases can be aided by the assessment of such cell states.

An aspect of the present invention relates to human papilloma virus (HPV), which induces benign epithelial proliferations of the skin and mucosa in humans and is associated with anogenital neoplasias and carcinomas. The intact DNA of HPV is supercoiled and thus resembles an endless loop of twisted telephone handset cord. Inside this shell, the viral DNA is packaged in and around proteins from the cell nucleus, histones, and associated peptides, into a structure that resembles cellular chromatin. (Turek, (1994)). Human papillomaviruses characterized to date are associated with lesions confined to the epithelial layers of skin, or oral, pharyngeal, respiratory, and, most importantly, anogenital mucosae. Specific human papillomavirus types, including HPV 6 and 11, frequently cause benign mucosal lesions, whereas other types, HPV 16, 18, and a host of other strains, are predominantly found in high-grade lesions and cancer. All human and animal papillomaviruses appear to share a similar genetic organization, although there are differences in the functions of individual viral genes and in their regulation. The most common genital HPV type associated with cervical carcinoma, HPV 16, has been studied most extensively.

All large open reading frames (ORFs) in HPV are on one DNA strand. Papillomaviral mRNAs appear to be transcribed solely from a single strand in infected cells. The viral genome can be divided into three regions, the upstream regulatory region (URR), or long control region (LCR), containing control sequences for HPV replication and gene expression, the viral early gene region, encoding, among others, the E2, E6 and E7 genes, and the late region, encoding the L1 and L2 genes. (Turek, (1994)).

HPV gene expression in high-grade premalignant disease or cancer appears restricted to the early genes, possibly due to cellular differentiation arrest induced by the viral E6 and E7 genes. In comparison to active HPV infection, E6 and E7 gene control in cancer is deranged by mutations in the viral URR and, in integrated viral fragments, by the disruption of the viral E2 gene, stabilization of E6 and E7 mRNAs, and influences at the cellular integration site.

Because the E2 gene is disrupted or inactivated in integrated HPV fragments in invasive cervical carcinomas (Cullen, (1991); Dürst, (1985); Matsukura, (1989); Schneider-Gädicke, (1986); Schwarz, (1985); Wilczynski, (1988)), it has been predicted that loss of E2 bestows a selective growth advantage to the infected cell because of uncontrolled E6 and E7 expression (Schneider-Gädicke, (1986); Schwarz, (1985)). Indeed, cervical cells containing replicating HPV genomes rapidly segregate and are outgrown in culture by cells that contain integrated viral genomes (Jeon (1995)), but the underlying mechanism(s) have remained unclear until recently. The full-length HPV 16 E2 gene products are strong transcriptional activators comparable to HPV 1 E2 at some viral as well as at simple, synthetic promoters (Demeret (1994); Ushikai (1994)).

Genes E6 and E7 are considered to have oncogenic activity. The encoded proteins interact with and disturb the physiologic functions of cellular proteins that are involved in cell cycle control. The E6/E7 proteins of HPV 16, 18 or related types are most efficient in this regard. Some of these activities lead to genetic instability of the persistently infected human cell. This enhances the probability of mutations in cellular proto-oncogenes and tumor suppressor genes and thus contributes to tumor progression. Mutations in cellular genes devoted to the intracellular surveillance of HPV infections, integration of viral DNA, and deletions or mutations of viral transcription control sequences lead to a significantly increased expression of the E6/E7 genes, which is a consistent characteristic of high-grade intraepithelial neoplasia and cancers. The genetic instability caused by viral oncoproteins and the autocatalytic increase in oncoprotein expression caused by mutations in the viral and cellular genome identify the virus as a major driving force of progression to carcinoma.

Individual types of human papillomaviruses (HPV) which infect mucosal surfaces have been implicated as the causative agents for carcinomas of the cervix, anus, penis, larynx and the buccal cavity, occasional periungal carcinomas, as well as benign anogenital warts. The identification of particular HPV types is used for identifying patients with premalignant lesions who are at risk of progression to malignancy. Although visible anogenital lesions are present in some persons infected with human papillomavirus, the majority of individuals with HPV genital tract infection do not have clinically apparent disease, but analysis of cytomorphological traits present in cervical smears can be used to detect HPV infection. Conventional viral detection assays, including serologic assays and growth in cell culture, are not commercially available and/or are not suitable for the diagnosis and tracking of HPV infection. Papanicolaou tests are a valuable screening tool, but they miss a large proportion of HPV-infected persons.

Thus, it is an object of the present invention to provide a method for assessing the stage of HPV-based disease.

It is another object of the present invention to provide an assay that can be combined with other assays to improve the accuracy and reliability of prognostic and diagnostic assessments of HPV-based disease.

It is a further object of the present invention to provide a method for assessing the risk that a patient infected with HPV will develop HPV-based disease.

It is another object of the present invention to provide a method for stratifying patients who are currently HPV-infected but without detectable HPV-based disease into those at risk for progression to disease and those not at risk for progression to disease.

It is also an object of the present invention to provide a method for identifying treatment regimes for patients having HPV-based disease.

Yet another object of the present invention to provide a method for monitoring the effectiveness of treatment of HPV-based disease.

A further object of the present invention to provide kits for assessing the stage of HPV-based disease.

Another object of the present invention to provide computer-based operation, analysis, and data management of assay data to assess the stage of HPV-based disease.

SUMMARY OF THE INVENTION

One embodiment of the present invention involves measuring the levels of expression of genes involved in a cell state, and comparing their expression to each other or to reference genes in a specific ratio, as an indication of the state of a disease in the cell sample. The present invention can be used to assess the stage or risk of a disease as indicated by the state of the cells. It can also be used to guide or assess the effectiveness of a therapy for a disease by identifying appropriate therapy based on the indicated cell state or by indicating any change in the state of cells subjected to the therapy.

In one form of the present invention, the stage and prognosis of a human papillomavirus (HPV) infection or HPV-based disease is assessed. This embodiment involves the measurement of the level of expression of two or more HPV genes. Genes for this purpose are the HPV E6, E7, L1, and E2 genes, although other HPV genes such as E1, E4, E5, and L2 can also be used. It has been discovered that the level of expression of these genes, the ratio of expression of these genes to each other or to reference genes, or both, are indicative of the stage of HPV-based disease.

Gene expression levels are used according to this invention to assess the progression of HPV infection from benign to malignant growth. HPV infection progresses from CIN I through CIN III and finally to malignant cancer. These stages can be identified by the ratios of HPV genes. In particular, the transition from CIN I to CIN II/III, i.e., a transition to pre-malignancy, can be predicted when the ratio of the present invention exceeds one. A ratio of greater than 3 in the present invention indicates a transition from pre-malignancy to malignant cancer. Thus, a ratio below 1 indicates a low-level of CIN in an HPV infected cell. A ratio between one and about three indicates a high grade CIN (i.e., CIN III) or pre-malignant condition. And a ratio of over about three is an indication of an HPV induced malignancy.

BRIEF DESCRIPTION OF THE DRAWINGS

FIG. 1 is a graph of detection of E6/E7 mRNA shown as the number of cells/well versus the number of E6/E7 mRNA/well.

FIG. 2 is a graph of the sensitivity of an HPV L1 assay shown as the number of RNA molecules/well versus the signal-to-noise ratio minus 1.

FIG. 3 is the probe sequence for HPV 16 L2 (SEQ ID NO: 1).

FIG. 4 is the probe sequence for HPV 16 L1 (SEQ ID NO: 2).

FIG. 5 is the probe sequence for HPV 16 E6/E7 (SEQ ID NO: 3).

FIG. 6 is the probe sequence for HPV 16 E2 (SEQ ID NO: 4).

FIG. 7 is the probe sequence for HPV 16 E4 (SEQ ID NO: 5).

DETAILED DESCRIPTION OF THE INVENTION

The present invention relates to the identification and monitoring of diseased cells. One method involves measuring the levels of expression of genes involved in a disease state, and comparing their expression to each other or to reference genes, as an indication of the state of the cells. Such measurements can be combined with other assays to increase the accuracy and reliability of the assessment of the disease state. One method of the present invention can be used to assess the stage of a disease as indicated by the state of the cells. This method can also be used to guide or assess the effectiveness of a therapy for a disease by identifying appropriate therapy based on the indicated disease state or by indicating any change in the state of cells subjected to the therapy.

Many diseases are characterized by specific cellular phenotypes and gene expression patterns. For example, neoplastic and cancerous cells generally exhibit certain distinctive morphologies and growth characteristics. Molecular characteristics, such as gene mutations and gene expression patterns are also a good indicator of disease progression. Virally infected cells can exhibit different morphologies and gene expression patterns, including expression of viral genes. Using the present invention, the characteristics of the cell state, such as changes in cell morphology or expression of genes can be determined from a patient sample.

The characteristics to be detected are generally specific to the cell state of interest and the disease suspected of being present in the cell sample. Such characteristics can be generally divided into two types, cytological characteristics and molecular characteristics. As used herein, cytological characteristics are characteristics such as, for example, overall cell shape and appearance. The primary identification and classification of many neoplastic and cancerous cells has traditionally been accomplished using cytological characteristics. Identification of cytological characteristics is generally slow, requires a relatively high level of training, and generally cannot be easily automated. As used herein, molecular characteristics are the presence and state of particular molecular species, such as proteins, nucleic acids, and metabolites. Such molecular characteristics are generally identified by detecting and measuring the particular molecules of interest.

The characteristics assayed can include additional or surrogate marker characteristics that are not a direct cause or result of the disease but that are related to certain disease and cell states. Examples of such additional markers include polymorphic markers, human leukocyte antigens (HLA) such as B7 that predispose women for cervical carcinomas, oncogenes, p53 mutations, other cancer markers, oncosupressors, cytokines, growth factor receptors, and hormones. Such markers can be present in, or absent from, cells exhibiting state- or disease-specific characteristics, and such presence or absence can be indicative of, for example, a more severe or less severe disease state. These markers can be used in conjunction with the disclosed method to infer either higher or lower risk of neoplastic disease depending on the number of abnormal scores or the magnitude of change in quantitative markers.

Examples of disease states for assessment using the present invention include, but are not limited to neoplasias and cancer. Disease states of interest are HPV-based disease—including HPV infection, cervical intraepithelial neoplasia (CIN), and cancer, atypical squamous cells of undetermined significance (ASCUS), warts, condylomata, epidermo dysplasia verruciformis and other skin diseases, laryngeal papilloma, oral papilloma and conjunctival papilloma.

An embodiment of the present invention is detection and measurement of the expression levels of certain HPV genes. An impressive amount of data has been accumulated over the past decade, showing that carcinoma of the cervix is associated with infection of certain types of HPV. Though the presence of HPV DNA in a precancerous lesion is indicative of an increased relative risk for cervical dysplasia and invasive carcinoma, it is still difficult to predict the clinical behavior of precancerous cervical lesions. Tumors arise due to the accumulation of genetic alterations which can activate oncogenes and/or inactivate tumor suppressor genes and/or genes involved in DNA damage recognition and repair.

The expression levels of E6 and E7 oncoproteins encoded by high-risk HPV types are a more sensitive and accurate measure of potential risk of an HPV infection developing into a cancerous lesion. The present invention measures the relative amounts of E6 and/or E7 expression levels and E2 and/or L1 in an HPV-infected lesion to determine the ratio of E6 and/or E7 to L1 and/or E2, where in this ratio is a direct measure of risk, and susceptibility to the development of a cancerous lesion. HPV expression can be measured by mRNA or protein levels in the cell.

In one aspect of the invention, the stage and prognosis of a human papillomavirus (HPV) infection or HPV-based disease is assessed. This embodiment of the present invention involves the measurement of the level of expression of one or more HPV genes discovered to be related to the stage and nature of HPV-based disease. Genes useful for this purpose include the HPV E6, E7, L1, and E2 genes. It has been discovered that the level of expression of these genes, the ratio of expression of these genes to each other or to one or more other genes, or both, are indicative of the stage of HPV-based disease. The level of expression is relative to other BPV genes, or the level of expression relative to a non-HPV gene, referred to herein as a reference gene. Such reference genes can be any appropriate gene (not encoded by HPV), and are, for example, housekeeping genes or other constitutively expressed genes. Examples of reference genes include actin genes, cytoskeletal genes, histone genes, tubulin genes, epidermal growth factor receptor genes, the normal p53 gene, the normal pRB gene, cyclin genes, β-globin genes, and glucose-6-phosphate dehydrogenase genes. Expression of reference genes can be measured in the same cell as the level of HPV genes are measured or in neighboring cells in the same cell sample. In such a case, the reference gene is an internal control for gene expression.

The relationship of the relative level of expression of these genes to the state of cells infected with HPV is generally illustrated in Table 1 below.

TABLE 1

| Medical Character | HPV-Based disease state | E6, E7, E6 + E7 | E2 | L1 |
|---|---|---|---|---|
| benign | HPV-infected normal tissue | low | low to high | low to undetectable |
| benign | Low grade CIN i.e., CIN I | low to medium | low to high | medium to high |
| neoplastic | High grade CIN i.e., CIN II/III | medium to high | low to undetectable | low to undetectable |
| neoplastic | Cancer | medium to high | low to undetectable | low to undetectable |

The HPV-based high grade CIN referenced in the table is the premalignant stage leading to cancer and low grade CIN is a productive viral infection that has little malignant potential but is a public health concern with respect to the spread of HPV infection. Normal tissue refers to cytologically normal tissue that is infected with HPV. Although not limited to this standard, one standard for establishing this lower limit of expression is a level below that detectable using the hybrid capture assay described in WO 93/10263 by Digene. As used herein, E6/E7 refers to E6, E7, or E6+E7. The addition of genes, as with "E6+E7," for example, refers to the combined expression of the added genes.

As can be readily discerned, each major disease state is represented by a unique expression pattern of these three sets of genes. Both of these conditions are regarded as serious medical aliments. Other relationships involving the relative level expression of other HPV genes (such as E1, E4, E5, and L2), and other, non-HPV genes, can also be used to assess cell state. For example, L2 and E4 are frequently associated with benign viral production diseases, and E1 is similar in profile to E2 and is often deleted in malignancies. Other relationships of expression for these HPV proteins can exist for other HPV-based diseases, and the disclosed method can be used to assess the state of such other diseases using the appropriate levels and ratios for that disease.

Using information about the levels and ratios of HPV genes in different cell states, the stage of the disease can be assessed in several ways. In some cases, the presence or absence of detectable expression is indicative of the disease state in the infected cells. For example, a lack of E2 expression (when HPV is present) is indicative of high grade CIN or cancer. In other cases, a change or difference in expression of an HPV gene product can be indicative of change occurring in the infected cell state. For example, an increased level of expression of E6 and E7—relative to, for example, an earlier sample or a reference sample—may be indicative of high grade CIN or cancer. A change in the ratio of E6/E7 expression to E2 expression is used to identify low grade CIN or a shift from normal cells to low grade CIN. Many other combinations of comparisons are also possible, and other combinations can be derived from the information in Table 1 for use in the method of the present invention.

One way in which ratios of HPV genes can be related to HPV-based disease states is by reference to groups of HPV genes. For this purpose, group 1 genes or gene sets include E6, E7, and E6+E7. Group 2 genes or gene sets include L1, L2, E4, and any combinations. Group 3 genes or gene sets include E1, E2, E5, and any combinations. Useful ratios of expression include ratios of members of group 1 to members of group 2 or group 3. Examples of theses ratios are (E6+E7)/(L1+L2), E6/L1, E7/L1, E6/L2, E7/L2, (E6+E7)/L1, (E6+E7)/L2), E6/(L1+L2), and E7/(L1+L2). For such ratios, a value of less than two is indicative of benign human papillomavirus infection or low grade intra-epithelial neoplasia. This type of infection is also classified as CIN I. HPV infections which progress beyond CIN I indicate cell transformation has occurred and cancerous growth has begun. These later infections (CIN II/III) have ratios of greater than 2. A ratio of expression of more than two is indicative of high grade intra-epithelial neoplasia or pre-malignant cancer. A ratio of expression of much more than two (i.e., exceeding 4 and up to infinity) is indicative of cancer. Preferred ratios for use in this invention are (E6+E7)/L1, (E6+E7)/(L1+L2), (E6+E7+E2+E4)/(L1+L2), (E6+E7)/(E2+E4), (E6+E7)/E2, (E6+E7+E2−E4)/(L1+L2).

There are several ways in which measured levels of expression of HPV genes can be compared and categorized. For example, where the presence or absence of expression is indicative of the cell state, expression of the HPV gene is analyzed without reference to the expression level of other genes. Where the relative level of expression of an HPV gene is indicative of the cell state, the measured level of expression is compared, for example, to the level of expression of the same type of HPV gene in a different cell sample (such as an earlier cell sample from the same source or reference cells harboring HPV), to the level of expression of a different type of HPV gene in the same or a different cell sample, to the level of expression of a non-HPV reference gene in the same cell sample, or to the level of expression of a non-HPV reference gene in reference cells.

In one embodiment of the present invention, levels and ratios of expression of HPV genes are compared to the levels of the same genes in a cell line that contains HPV (such as HeLa or CaSki). Such cell lines provide a standard against which levels of expression of HPV genes in cell samples are compared. Such comparisons are used to assess and compare the absolute levels of expression of these HPV proteins with those in a standard or comparative cell line. Other cell lines useful for this purpose are non-cancerous cell lines infected with HPV 16 (such as W12) or HPV 31 (such as CIN-612; Meyers (1992)).

The levels and ratios of expression of HPV genes are also compared to reference genes, such as housekeeping genes or other constitutively expressed genes, in the same cells or in reference cells, such as a cell line. For example, the level of expression of the HPV gene and the reference gene is measured in the same cell sample. Such measurements provide an internal control of the overall expression level in a cell sample and are used to calculate a corrected level of expression for the HPV gene to allow more accurate comparisons of the level of expression between different cell samples. One form of correction is referred to as normalization. Thus, the level of expression of one or more HPV genes can be measured in two or more cell samples along with the level of expression of the same reference gene in each of the cell samples. The level of expression of the HPV genes is then normalized to each other based on differences, if any, between the measured level of expression of the reference gene in each of the samples.

In some stages of HPV-based disease, the expression of a particular HPV gene is low or undetectable. Such lack of detectable expression is used herein to identify patterns of expression that serve as prognostic or diagnostic indicators. The expression of other HPV genes is assessed in parallel or in the same assay to provide a control for the lack of expression of one or more of the genes to be assessed. This is accomplished by measuring the expression of the several HPV genes together or in parallel. For example, measuring the level of expression of the HPV E6, E7, L1, E4, and E2 genes in parallel is useful since at least one of these genes is expressed in all of the stages of HPV-based disease. In a preferred embodiment of the present invention, a ratio of E6/E7 to L1/E2 provides an indicator of likelihood of developing cancer from the HPV infection. In this way, indicative information is collected as well as providing an internal control. The presence of L1, L2, and E4 in combination is also indicative of benign disease while the absence of E1 and/or E2 is indicative of neoplastic potential.

The types of comparison described above can also be used with other genes and other disease states. That is, the measured level of expression of a gene of interest can be compared, for example, to the level of expression of the same type of gene in a different cell sample (such as an earlier cell sample from the same source or appropriate reference cells), to the level of expression of a different type of gene in the same or a different cell sample, to the level of expression of a reference gene in the same cell sample, or to the level of expression of a reference gene in reference cells.

Expression of genes of interest, such as the HPV E6, E7, L1, E4, and E2 genes, can be assessed using any suitable method. For example, RNA can be detected using hybridization, amplification, or sequencing techniques, and protein can be detected using specific antibodies. Many techniques for the specific detection of gene expression, by detection of expression products, are known and can be used with the disclosed method. One technique for detecting and measuring the level of expression of genes of interest is detection of RNA transcribed from the genes of interest. For the most reliable comparisons, expression levels that are to be compared should be measured using the same technique and be performed in the same manner.

For hybridization detection of HPV nucleic acids, a mixture of probes specific for these sequences from different HPV types can be used. This ensures that the method will detect expression regardless of the type of HPV involved. For some purposes, it may be desirable to use probes designed for the sequence of a certain HPV type, or a mixture of probes for only some HPV types. Such probes may or may not be type-specific depending on the differences between the sequences of the HPV nucleic acids to be detected. One useful mixture for this purpose would include probes for HPV types more closely associated with a progression to cancer. The HPV types most commonly associated with cervical cancer are types 16 and 18.

Useful techniques for measuring the level of expression of a gene of interest in a cell sample include the hybrid capture technique described in WO 93/10263 by Digene, PCR in situ hybridization techniques described by (Nuovo, 1997)), branched DNA assays (Chernoff (1997)), transcription-mediated amplification (TMA); Stoflet (1988)), and polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, (1991); Landegren, (1993)).

Numerous assays for the detection and measurement of gene expression products are known and can be adapted for the determination of the level of expression of genes of interest in the disclosed assay. For example, many of the techniques for the detection of HPV in general or expression of other HPV genes described below can also be adapted for use in the disclosed assay for the detection of expression of HPV genes E6, E7, L1, E4, and E2.

Many HPV detection and typing assays, which can be used in the disclosed method, are known, including assays involving Southern blots, dot blots, in situ hybridization, polymerase chain reaction, and solution hybridization. Mant (1997) describes PCR assays used to identify DNA from specific HPV types. Cope (1997) describes a PCR-based test using a consensus primer and a Hybrid Capture assay (HCA) of detection of HPV types. The hybrid capture assay is also described in WO 93/10263 by Digene. The hybrid capture assay is a useful method for detection of HPV and for determining HPV type in combination with the disclosed assay.

Swan (1997), discloses an HPV detection assay exploiting the 5' to 3' exonucleolytic activity of Taq DNA polymerase to increase the signal from fluorescent dyes by releasing them from genotype-specific probes during PCR. Lizardi (1997), describes a method of detecting HPV using in situ hybridization with non-radioactive probes and visualization with conventional bright-field or fluorescence microscopy, or laser scanning confocal microscopy. Zehbe [1] (1997), describes a modified version of in situ hybridization for detection of HPV that involves signal amplification. Leiserowitz (1997), describes use of reverse transcriptase-polymerase chain reaction to detect HPV. Zehbe [2] (1997), describes a nonisotopic, enzyme-linked immunosorbent assay-based sandwich capture hybridization assay for HPV detection.

In one embodiment of the present invention RNA was analyzed directly by solution based procedures. The cells were first lysed by adding a proteolytic enzyme to the cells contained in wells of a microtiter plate. Non-limiting examples of enzymes for use in the present invention include proteinase K or Pronase. Cells can also be subjected to detergent lysis or osmotic lysis or a French Press. After incubation, biotinylated DNA probes were added to each well. The RNA:DNA hybrids were captured onto a solid phase by transferring to streptavidin coated microplates. Alkaline phosphatase-conjugated antibodies to RNA:DNA hybrids were added to each well in the hybridization microplate and signals were generated by adding a chemiluminescent reagent such as CDP-Star® with Emerald II (Tropix) to each well. The signal was read from the microplate. The solution based DNA analysis was performed similarly to the RNA analysis except that the microtiter plates were coated with anti-RNA:DNA hybrid antibodies and the probes were RNA probes.

Other methods for detection and assessment of HPV infections that can be used in the disclosed method are described in U.S. Pat. Nos. 5,415,995, 4,777,239, 5,484,699, 4,983,728, 5,527,898, 5,364,758, 5,639,871, 5,501,947, 5,665,533, 4,748,109, 5,623,932, 5,665,571 and 5,648,459. These are just examples of HPV detection and typing assays that may be used in combination with the disclosed molecular assay. Many of the techniques described above can also be adapted for use in the disclosed assay for the detection of expression of HPV genes.

The disclosed assay and other assays can also be sequentially combined. That is, first one type of assay can be performed, and then, depending on the results, another assay can be performed. For example, an assay to detect HPV (or HPV type) can be performed first, then, if HPV is present, the disclosed molecular assay can be performed. As another example, the disclosed molecular assay can be performed first, and if the results of the assay were indicative of a high grade CIN or cancer, a cytological assay or biopsy can be performed. Such sequential combinations are particularly useful for limiting more extensive testing to patients and samples that are identified as high risk.

Useful sequential orders for the assays are (1) an HPV assay, followed by an assay for one or more other markers, followed by a cytological or histological assay; (2) a cytological or histological assay, followed by an HPV assay or an assay for one or more other markers, followed by an HPV assay or an assay for one or more other markers (whichever had not been performed first); (3) a cytological or histological assay, followed by a combined or simultaneous HPV and marker assay; (4) a combined or simultaneous HPV and marker assay, followed by a cytological or histological assay; and (5) detection of HPV, detection of HPV type, an HPV assay, and a cytological or histological assay. Each combination of assays is followed by an assessment, using the combined assay results, of the cell state, disease state, patient status, patient prognosis, or other assessment as described herein.

Where the results of initial assays are either equivocal or suggest a more severe stage of disease, further assays are useful to clarify and confirm the initial results. For example, where a cell sample is a mosaic with some cells benignly infected with HPV and others exhibiting high grade neoplasia or cancer, an assay measuring expression of HPV genes may give equivocal results. By following up with a morphological assay, the presence of the high grade neoplastic or cancerous cells can be established. In this case, the benefit of the disclosed method is that only some of the cell samples assayed (those with either equivocal or severe results) need be tested further.

The disclosed method can also be combined with treatment regimes. For example, results in the disclosed assay or method indicative of high grade CIN or cancer suggest that antiviral therapy will be ineffective since these stages of disease are often accompanied by integration of HPV into the genome. On the other hand, assay or method results indicative of normal or low grade stages of disease suggest antiviral treatments since HPV is generally not integrated at these stages. Antiviral treatments include, for example, drugs or therapeutic vaccines. Where results of the disclosed method indicate a benign cell state, treatment can be avoided altogether. The ability to make such assessments reliably and accurately is a significant benefit of the disclosed assay.

The disclosed method can include the combination of a molecular assay as described above with any other assay for assessing a disease or state of cells in a cell sample. For example, a molecular assay measuring the level or ratio of expression of HPV genes can be combined with cytological assays, histological assays, determination of the HPV type present, determination of the level of HPV present, assays detecting other cellular markers such as oncoproteins or tumor suppressors, or combinations of these assays. Such assays are known and are used for the diagnosis of HPV infection or HPV-based disease and assessment of the stage of disease. Results from a molecular assay and one or more additional assays can be combined to increase the reliability of any assessment, prognosis, diagnosis, or monitoring of HPV-based disease. This possibility of combination is a particularly useful aspect of the disclosed method since the HPV molecular assays described above provide information about HPV-based disease that is distinct from other assays. Where multiple assays point in the same prognostic or diagnostic direction, the reliability of the assessment is increased. Useful combinations include a cytological assay and the disclosed molecular assay, an assay for determining HPV type and the disclosed molecular assay, and a combination of a cytological assay, a typing assay, an assay for detecting cancer markers, and the disclosed molecular assay. Combined assays can be performed in any order and in any temporal relationship. For example, various assays can be performed in parallel or simultaneously. Such assays can be performed in any manner such as on the same apparatus by the same person, with different apparatus, or in the same or different locations.

Cytological assays for use in assessing the stage of HPV-based disease are known and can be used in the disclosed method. The well established Pap smear and Hematoxylin & Eosin stains (H&E) are preferred examples. The use and analysis of Pap smears and H&E stains are well-known in the art.

A cell sample as the term is used herein is primarily a collection of cells from a patient. One method of obtaining cells is through non-invasive means, which is defined herein as obtained without the puncturing of a patient. Examples of non-invasive means are, for example, cell samples obtained from urine or a nasal, epithelial, cervical or other cell surface scrape. Patient cells can also be obtained by other means including, for example, needle biopsy or tissue biopsy.

The cell sample can be preserved in a collection medium which allows for a combination of two or more assays of different characteristics related to a cell state of interest. As used herein, the assay or assays refer to detection or measurement of specific characteristics, the results of which may be combined with other such measurements of other characteristics to an overall assessment of a cell suspected of being infected with one or more diseases. These assays may include, for example, a combination of morphological analysis and quantitation of a particular RNA or DNA or protein whose levels provide a specific indication of the presence or progression of a disease. Alternatively, for example, the collection medium can be used to combine an assay identifying the morphology of cells in a cell sample with one or more assays identifying the HPV type involved, and, for example, identifying whether the HPV type identified is a high risk or low risk HPV type for the development of HPV-induced cell transformation and cancer.

For example, sources of cell samples for assessing HPV-based disease include cervix, vagina, vulva, anus, penis, larynx, buccal cavity, lymph nodes, malignant deposits in any part of the human body, and epidermis; all of which are known sites of HPV infection and pathology.

Cell samples for use in the present invention can be collected and stored in liquid medium. Examples of useful cell collection media are STM (Digene), PreservCyt® (Cytyc), and CytoRich™ (Autocyte). These media (PreservCyt® and CytoRich™) were developed for the collection of cytological samples but can be adapted for use with molecular assays.

Cell samples for use in the method of the present invention can be fixed or processed in any manner consistent with the assays to be performed. For example, both cytological and molecular assays can be performed using cells fixed on a solid substrate such as, for example, a slide. The requirements of the assays to be performed will generally identify the sample processing to be used.

The present invention can be conveniently performed using kits that include one or more of the materials needed for the method, such as reagents and sample collection and handling materials. For example, kits can include cell collection medium, sample preserving reagents, reagents for specific detection of DNA and/or expression products (RNA or proteins) of one or more of the E2, E4, E5, E6, E7, L1 or L2 genes, and sample handling containers. Useful reagents for detection of expression of the HPV genes are nucleic acid probes for those genes. A kit may also contain control samples or reagents, or reagents and materials for performing other assays to be combined with the disclosed assay. In addition, the kits can contain reagents for the separation of RNA and/or DNA from other cellular components.

The present invention can be performed using devices adapted to the method. Numerous devices for performing similar assays are known and in use and can be adapted for use with the disclosed assays and method. For example, devices are known for automating all or a part of sample assays and sample handling in assays.

All or part of the disclosed method can be controlled or managed using special purpose computer programs. The data collected from the disclosed method, and data from any other assay used in combination, can be compiled, analyzed, and output in various forms and for various purposes using special purpose computer programs. Such programs can be used with, or combined into, other patient or data management computer programs. The usefulness of such a program increases with the number of measurements or assessments to be combined, and the relative importance of each type of measurement to the overall assessment. Computer programs for use with the disclosed method can be used on general purpose computers, or can be incorporated into special purpose computers or computerized devices for controlling the disclosed method, handling and analyzing data from the disclosed method or both.

EXAMPLES

The examples herein are meant to exemplify the various aspects of carrying out the invention and are not intended to limit the invention in any way.

Example 1

General Methods for Nucleic Acid Analysis

The assay for nucleic acids follows in general principle the method for detecting HIV RNA by the Digene Hybrid Capture HIV Test, described in WO 93/10263 by Digene. Briefly, following lysis, 50 µl of probe mix (containing DNA biotinylated probe) was added to each well. The plate was sealed and incubated at 65° C. for 2 hours for hybridization to occur. After hybridization, samples were transferred to a strepavidin-coated microplate, and 25 µL of anti-hybrid antibody was added to each well. The plate was agitated at 1100 RPM, for 1 hour, at room temperature. Wells were washed 6× times with 65° C. wash buffer, followed by one wash using distilled water. 100 µl of a chemiluminescent substrate was added to each well and the plate was incubated at room temperature for 30 minutes. The plate was then read in the DML 2000 luminometer. The data was then expressed as signal-to-noise. Using a calibration curve, the chemiluminescent signal generated by each specimen was converted into mRNA copies per cell. The assay described above can be run on either whole lysed cells or nucleic acid separated from other cellular components.

Example 2

Quantitation of HPV

This example illustrates the measurement of HPV E6/E7 expression for use in the disclosed method. A method for detecting and quantitating HPV mRNA, including E6/E7 and mRNA has been developed. This example measures expression in CaSki cells, but the method is generally applicable to other cell lines and clinical specimens. CaSki cells contain an integrated high-risk HPV-16 genome (about 600 copies/cell). CaSki cells were maintained in subconfluence in RMPI 1640 media containing 10% FBS and 10 mM sodium pyruvate. For this example, CaSki cells were grown to confluence and were removed from the dishes by treatment with 0.1% trypsin-0.5 mM EDTA. Using trypan blue, viable cells were counted under microscopy. Cells were seeded, in 10 µl volumes, at final concentrations of 10, $10^2$, $10^3$, $10^4$, and $10^5$ cells/well in a polystyrene, tissue culture treated, 96 well plate. Each dilution was performed and seeded in triplicate.

The cells were lysed with Proteinase K (30 units) in a Tris-EDTA-buffered SDS). The plate solutions (20 mM Tris pH 7.4, 20 mM EDTA and 0.5' was sealed, agitated for 30 seconds at 1100 RPM and incubated at 37° C. for 30 minutes. The test for HPV mRNA follows in general principle the method for detecting HIV RNA by the Digene Hybrid Capture HIV Test, described in WO 93/10263 by Digene. Briefly, following lysis, 50 µl of probe mix (containing E6/E7 DNA biotinylated probe) was added to each well. The plate was sealed and incubated at 65° C. for 1.5 hours for hybridization to occur. After hybridization, samples were transferred to a strepavidin-coated microplate, and 25 µl of anti-hybrid antibody was added to each well. The plate was agitated at 1100 RPM, for 1 hour, at room temperature. Wells were washed 6× times with 65° C. wash buffer, followed by one wash using distilled water. 100 µl of a chemiluminescent substrate was added to each well and the plate was incubated at room temperature for 30 minutes. The plate was then read in the DML 2000 luminometer. The data was then expressed as signal-to-noise. Using a calibration curve, the chemiluminescent signal generated by each specimen was converted into mRNA copies per cell. The data for the direct detection of HPV mRNA from CaSki cells is shown in FIG. 1. This method is exemplified by the detection and quantitation of E6/E7 mRNA, but has also been applied to quantitate other mRNA molecules (for example, HPV L1 mRNA) from CaSki cells (FIG. 2).

Example 3

Quantitation of HPV mRNA Using Preservative Collection Medium

CaSki cell line was trypsinized by incubating with 0.25% Trypsin-EDTA for 5 minutes at 37° C. Cells were pelleted from the suspension by centrifugation at 800 rpm for 3 minutes in Sorvall RT 6000 centrifuge. Cell pellet was resuspended in 500 µl of 1× PBS and counted under microscope Trypan Blue solution. Cells were diluted to 50 and 500 cells/µl in 1× PBS. 10 µl of each cell concentration, including zero point (10 µl of 1× PBS) were spiked in 3 ml of PreservCyt reagent. 100 µl of Sample Conversion Buffer were added into each tub to help visualize the cell pellet. All samples were mixed well and were spun down at 3800 rpm for 15 minutes in Sorvall RT 6000 centrifuge. Supernatants were discarded and tubes were drained by inversion on the Kimtowels for 2 to 5 minutes on the bench. All pellets were resuspended with 50 µl of the lysis reagent (50 units of Proteinase K) and mixture was transferred into the plate coated with streptavidin. Plate was covered with the plate sealer and was incubated at 37° C. for 30 minutes (heat block) with agitation every 15 minutes.

50 µl of each E6/E7 RNA calibration were loaded in designated wells at 0, $10^3$, $10^4$, $10^5$, $10^6$, $10^7$ and $10^8$ molecules/well to construct calibration curve for mRNA in the specimen. 50 µl of the probe mix was added into each well. Plate was covered with the plate sealer and was agitated for 1 minute at 1100 rpm on the bench top shaker. Samples were incubated at 65° C. for 1.5 hours (hybridization reaction) in the heat block. Plate was transferred into the bench top shaker and was incubated for 1 hour with agitation at 1100 rpm at room temperature (capture reaction). 25 µl of Detection Reagent 1 was added into each well and plate was incubated without agitation for 1 hour at room temperature.

The contents of the plate were discarded and the plate was washed vigorously six times with Wash Buffer at 65° C. and one time with deionized water at room temperature. The plate was drained into Kimtowels and 100 µl of the Detection Reagent 2 was added into each well. Plate was incubated for 30 minutes at room temperature covered from the light. At the end of incubation time, plate was read on the Digene DML 2000 luminometer and the data were expressed as signal-to-noise.

Example 4

Comparison of the Expression of E6/E7 RNA and L1 RNA in Cell Lines Containing Episomal and Integrated HPV 16 DNA Cell Lines Tested The following cell lines were examined according to the procedures outlined above.

HaCaT: an immortalized human keratinocyte cell line (Boukamp (1988))

SiHa: a human cancer cell line (Friedl, (1970))

W12: a non-tumorigenic human cervical keratinocyte cell line (Stanley, (1989))

HPV Infection Status

HaCaT cells were infected with HPV 16 by the procedure of White et. al. (White (1998)) to produce an episomal (non-integrated, total sequence, not spliced) HPV infection. Approximately 1 copy of HPV16 was present for every 40 cells. These cells are considered a representative of early stage infection or CIN I (cervical intraepithelial neoplasia). W12 cells contain approximately 100 copies of episomal HPV16 DNA and represent pre-malignant, immortalized cells or CIN II or CIN III. SiHa cells contain 1-2 copies of HPV16 integrated into the genome. These cells are considered to represent cancer.

Procedure

The RNA analysis was done according to Example 1 or the following procedure. Single stranded, biotinylated, DNA probes containing the specific HPV16 gene sequences were prepared. For HaCaT and SiHa cell lines, cells were grown to confluency, cells were harvested, and the total RNA was purified using the RNeasy kit (Qiagen Inc., Santa Clarita, Calif.). For W12, whole cells were used for analysis. RNA calibrators containing the complete HPV genome were prepared by transcribing (+) sense RNA from a plasmid containing the complete HPV16 genome with T7 RNA polymerase. The RNA was then diluted to $10^3$, $10^4$, $10^5$, $10^6$, and $10^7$ copies per 50 µl. Aliquots of cellular RNA were diluted to 50 µl and then 50 µl of Probe mix (containing the biotinylated, single-stranded DNA probe) was added and hybridized to the RNA specimens for 2 hours at 65° C. The hybridization reactions were transferred to a streptavidin coated microplate and 25 µl of Detection Reagent 1 was added to each well. (Detection Reagent 1 contains the alkaline-phosphatase—anti-RNA:DNA monoclonal antibody conjugate.) During a 1 hour incubation with shaking, RNA:DNA hybrids were captured onto the streptavidin coated plate and were simultaneously reacted with the anti-hybrid antibody conjugate. After several wash steps, a chemiluminescent substrate (Tropix CDP-star with Emerald) was added to the wells, and the light output was measured in a microplate luminometer after 30 minutes incubation at room temperature.

Quantitation

The quantitation of HPV mRNA was performed as follows. The results from the RNA calibrators were used to construct standard curves. The regression equation was calculated from the logarithm of the copies versus the logarithm of signal to noise minus one [(S/N)−1]. The regression equations were then used to calculate the number of copies of mRNA in the cellular RNA samples.

Ratio Results

The ratios of HPV 16 E6, E7, E2, E4, L1 and L2 were calculated for each cell type. The results are shown in Table 2. These results demonstrate that in an episomal, early stage infection the ratio of (E6+E7)/L1 is about 0.7, in the pre-malignant immortalized cell line the ratio is about 4 and in the cancerous cell line the ratio approaches infinity.

TABLE 2

|  | HaCaT | W12 | SiHa |
| --- | --- | --- | --- |
| HPV Status | Episomal | Episomal | Integrated |
| Cell Status | Early stage infection | Pre-malignant, immortalized | Malignant |
| (E6 + E7)/L1 | 0.68 | 4.00 | ∞* |
| (E6 + E7)/(L1 + L2) | ND | 3.47 | 59.9 |
| (E7 + E6 + E2 + E4)/(L1 + L2) | ND | 6.96 | 70.6 |
| (E6 + E7)/(E2 + E4) | ND | 1.00 | 5.60 |
| (E6 + E7)/E2 | ND | 4.40 | 12.00 |
| (E6 + E7 + E2 − E4)/(L1 + L2) | ND | 1.58 | 59.10 |

*L1 gene transcripts were undetectable in SiHa cells. Therefore, ratios of other gene transcripts to the L1 gene transcript are infinitely large.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

Birkenmeyer & Mushahwar, *J. Virol. Meth.*, 35:117-126 (1991)
Boukamp, et al., *J. Cell Biol.* 106:761-771 (1988).
Chernoff et al. *J. Clinical Microbiology* 35(11):2740-2744 (1997)
Cope et al. *J. Clin. Microbiol.* 35(9):2262-2265 (1997)
Cullen et al., *J. Virol.* 65(2):606-612 (1991)
Demeret et al., *J. Virol.* 68(1):7075-7082 (1994)
Dürst et al., *J. Gen. Virol.* 66:1515-1522 (1985)
Friedl et al., *Proc. Soc. Exp. Biol. Med.* 135(3):543-5 (1970)
Jeon et al., *J. Virol.* 69(5):2989-2997 (1995)
Kongsamul et al., *Biochem. Biophys. Res. Commun.* 127 (1):71-9 (1985).
Landegren, *Trends Genetics,* 9(6):199-204 (1993)
Leiserowitz et al. *Gynecol. Oncol.* 66(2):295-299 (1997)
Lizard et al. *Histochem J.* 29(7):545-554 (1997)
Mant et al. *J. Virol. Meth.* 66(2):169-178 (1997)
Matsukura et al., *Virology* 172(1):63-72 (1989)
Meyers et al., *Science* 14; 257:971-3 (1992)
Nuovo, *PCR In Situ Hybridization: Protocols and Applications,* 3rd Edition, Lippencott-Raven Publishers, Philadelphia 1997
Pattillo et al., *Science* 196(4297):1456-8 (1977).
Schneider-Gädicke et al. *EMBO J.* 5:2285-2292 (1986)
Schwarz, et al., *Nature* 314:111-114 (1985)
Stanley et al., *Int. J. Cancer* 15;43(4):672-6 (1989)
Stoflet et al. *Science* 239:491-494 (1988)
Swan et al. *J. Clin. Microbiol.* 35(4):886-891 (1997)
Turek, *Adv Virus Res.* 44:305-356 (1994)
Ushikai et al., *J. Virol.* 68(1):6655-6666 (1994)
White et al., *J. Virol.* 72(2): 959-964 (1998).
Wilczynski et al., *Virology* 166:624-267 (1988)
Zehbe (1) et al. *Am. J. Pathol.* 150(5): 1553-1561 (1997)
Zehbe (2) et al. *Mod. Pathol.* 10(3):188-91(1997)

We claim:

1. A method of diagnosing risk of HPV 18-induced neoplasia comprising the steps of:
   quantifying a first level of one or more HPV 18 mRNA from a sample collected from a patient infected with HPV, wherein the one or more HPV 18 mRNA is selected from the group consisting of E2 mRNA, E4 mRNA, E6 mRNA, and E7 mRNA;
   quantifying a second level of one or more HPV 18 mRNA from a sample collected from said patient, wherein the one or more HPV 18 mRNA is selected from the group consisting of E2 mRNA, L1 mRNA, and L2 mRNA; and
   determining a ratio of the quantified first and second levels of HPV 18 mRNA, wherein the ratio is selected from the group consisting of (E6+E7)/L1, (E6+E7)/(L1+L2), (E2+E4+E6+E7)/(L1+L2), and (E6+E7)/E2,
   wherein a ratio of greater than 2 is indicative of HPV 18-induced cell transformation and risk of neoplasia.

2. The method of diagnosing risk of HPV 18-induced neoplasia of claim 1, wherein the determined ratio is (E6+E7)/L1.

3. The method of diagnosing risk of HPV 18-induced neoplasia of claim 1, wherein the determined ratio is (E6+E7)/(L1+L2).

4. The method of diagnosing risk of HPV 18-induced neoplasia of claim 1, wherein the determined ratio is (E2+E4+E6+E7)/(L1+L2).

5. The method of diagnosing risk of HPV 18-induced neoplasia of claim 1, wherein the determined ratio is (E6+E7)/E2.

6. A method of diagnosing the onset of HPV 18-induced neoplasia comprising the steps of:
   quantifying a level of a group 1 HPV 18 mRNA from a sample collected from a patient infected with HPV 18;
   quantifying a level of a group 2 HPV 18 mRNA from a sample collected from said patient; and
   determining a ratio of the quantified levels of the group 1 mRNA to group 2 mRNA,
   wherein a ratio of greater than 2 is indicative of HPV 18-induced neoplastic onset.

7. A method of diagnosing the risk or onset of HPV 18-induced neoplasia comprising the steps of:
   quantifying a level of a group 1 HPV 18 mRNA from a sample collected from a patient infected with HPV 18;
   quantifying a level of a group 3 HPV 18 mRNA from a sample collected from said patient; and
   determining a ratio of the quantified levels of the group 1 mRNA to group 3 mRNA,
   wherein a ratio of greater than 2 is indicative of high risk or onset of HPV 18-induced neoplastic onset.

8. A method of diagnosing the risk or onset of HPV 18-induced neoplasia comprising the steps of:
   quantifying a level of a group 1 HPV 18 mRNA from a sample collected from a patient infected with HPV 18;
   quantifying a level of a group 2 HPV 18 mRNA from a sample collected from said patient;
   quantifying a level of a group 3 HPV 18 mRNA from a sample collected from said patient; and
   determining a ratio of the quantified level of the group 1 mRNA to the sum of the quantified levels of the group 2 mRNA and the group 3 mRNA,
   wherein a ratio of greater than 2 is indicative of high risk or onset of HPV 18-induced neoplastic onset.

9. A method of diagnosing a stage of HPV 18-induced disease comprising the steps of:
   quantifying a first level of one or more HPV 18 mRNA from a sample collected from a patient infected with HPV 18, wherein the one or more HPV 18 mRNA is selected from the group consisting of E6 mRNA and E7 mRNA;

quantifying a second level of one or more HPV 18 mRNA from a sample collected from said patient, wherein the one or more HPV 18 mRNA is selected from the group consisting of L1 mRNA, L2 mRNA, and E2 mRNA; and determining a ratio of the quantified first and second levels of HPV 18 mRNA, wherein the ratio is selected from the group consisting of E6/L1, E6/L2, E6/E2, E6/(L1+L2), E6/(L1+E2), E6/(L2+E2), E6/(L1+L2+E2), E7/L1, E7/L2, E7/E2, E7/(L1+L2), E7/(L1+E2), E7/(L2+E2), E7/(L1+L2+E2), (E6+E7)/L1, (E6+E7)/L2, (E6+E7)/E2, (E6+E7)/(L1+L2), (E6+E7)/(L1+E2), (E6+E7)/(L2+E2), and (E6+E7)/(L1+L2+E2), wherein any ratio of greater than 2 is indicative of early stage HPV 18-induced disease, thereby diagnosing a stage of HPV 18-induced disease in a patient infected with HPV.

10. The method of diagnosing a stage of HPV 18-induced disease of claim 9, wherein the determined ratio is E6/L1.

11. The method of diagnosing a stage of HPV 18-induced disease of claim 9, wherein the determined ratio is E6/L2.

12. The method of diagnosing a stage of HPV 18-induced disease of claim 9, wherein the determined ratio is E6/E2.

13. The method of diagnosing a stage of HPV 18-induced disease of claim 9, wherein the determined ratio is E6/(L1+L2).

14. The method of diagnosing a stage of HPV 18-induced disease of claim 9, wherein the determined ratio is E6/(L1+E2).

15. The method of diagnosing a stage of HPV 18-induced disease of claim 9, wherein the determined ratio is E6/(L2+E2).

16. The method of diagnosing a stage of HPV 18-induced disease of claim 9, wherein the determined ratio is E6/(L1+L2+E2).

17. The method of diagnosing a stage of HPV 18-induced disease of claim 9, wherein the determined ratio is E7/L1.

18. The method of diagnosing a stage of HPV 18-induced disease of claim 9, wherein the determined ratio is E7/L2.

19. The method of diagnosing a stage of HPV 18-induced disease of claim 9, wherein the determined ratio is E7/E2.

20. The method of diagnosing a stage of HPV 18-induced disease of claim 9, wherein the determined ratio is E7/(L1+L2).

21. The method of diagnosing a stage of HPV 18-induced disease of claim 9, wherein the determined ratio is E7/(L1+E2).

22. The method of diagnosing a stage of HPV 18-induced disease of claim 9, wherein the determined ratio is E7/(L2+E2).

23. The method of diagnosing a stage of HPV 18-induced disease of claim 9, wherein the determined ratio is E7/(L1+L2+E2).

24. The method of diagnosing a stage of HPV 18-induced disease of claim 9, wherein the determined ratio is (E6+E7)/L1.

25. The method of diagnosing a stage of HPV 18-induced disease of claim 9, wherein the determined ratio is (E6+E7)/L2.

26. The method of diagnosing a stage of HPV 18-induced disease of claim 9, wherein the determined ratio is (E6+E7)/E2.

27. The method of diagnosing a stage of HPV 18-induced disease of claim 9, wherein the determined ratio is (E6+E7)/(L1+L2).

28. The method of diagnosing a stage of HPV 18-induced disease of claim 9, wherein the determined ratio is (E6+E7)/(L1+E2).

29. The method of diagnosing a stage of HPV 18-induced disease of claim 9, wherein the determined ratio is (E6+E7)/(L2+E2).

30. The method of diagnosing a stage of HPV 18-induced disease of claim 9, wherein the determined ratio is (E6+E7)/(L1+L2+E2).

31. A method of diagnosing HPV 18-induced cancer comprising the steps of:

quantifying a first level of one or more HPV 18 mRNA from a sample collected from a patient infected with HPV, wherein the one or more HPV 18 mRNA is selected from the group consisting of E6 mRNA and E7 mRNA;

quantifying a second level of one or more HPV 18 mRNA from said patient, wherein the one or more HPV 18 mRNA is selected from the group consisting of E2 mRNA, E4 mRNA, L1 mRNA and L2 mRNA; and determining a ratio of the quantified first and second levels of HPV 18 mRNA, wherein the ratio is selected from the group consisting of (E6+E7)/L1, (E6+E7)/(L1+L2), and (E6+E7)/(E2+E4), wherein a ratio of greater than 4 is indicative of HPV 18-induced cancer.

32. The method of diagnosing HPV 18-induced cancer of claim 31, wherein the determined ratio is (E6+E7)/L1.

33. The method of diagnosing HPV 18-induced cancer of claim 31, wherein the determined ratio is (E6+E7)/(L1+L2).

34. The method of diagnosing HPV 18-induced cancer of claim 31, wherein the determined ratio is (E6+E7)/(E2+E4).

35. A method of diagnosing the risk or onset of HPV 18-induced cancer comprising the steps of:

quantifying a group 1 HPV 18 mRNA from a sample collected from a patient infected with HPV;

quantifying a group 2 HPV 18 mRNA from a sample collected from a patient infected with HPV; and determining a ratio of group 1 mRNA level to group 2 mRNA level;

wherein any ratio of greater than 4 is indicative of high risk or onset of HPV 18-induced cancer.

36. A method of diagnosing the risk or onset of HPV 18-induced cancer comprising the steps of:

quantifying a group 1 HPV 18 mRNA from a sample collected from a patient infected with HPV;

quantifying a group 3 HPV 18 mRNA from a sample collected from a patient infected with HPV; and determining a ratio of group 1 mRNA level to group 3 mRNA level;

wherein any ratio of greater than 4 is indicative of high risk or onset of HPV 18-induced cancer.

37. A method of diagnosing risk of HPV 31-induced neoplasia comprising the steps of:

quantifying a first level of one or more HPV 31 mRNA from a sample collected from a patient infected with HPV, wherein the one or more HPV 31 mRNA is selected from the group consisting of E2 mRNA, E4 mRNA, E6 mRNA, and E7 mRNA;

quantifying a second level of one or more HPV 31 mRNA from a sample collected from said patient, wherein the one or more HPV 31 mRNA is selected from the group consisting of E2 mRNA, L1 mRNA, and L2 mRNA; and determining a ratio of the quantified first and second levels of HPV 31 mRNA, wherein the ratio is selected from the group consisting of (E6+E7)/L1, (E6+E7)/(L1+L2), (E2+E4+E6+E7)/(L1+L2), and (E6+E7)/E2, wherein a ratio of greater than 2 is indicative of HPV 31-induced cell transformation and risk of neoplasia.

38. The method of diagnosing risk of HPV 31-induced neoplasia of claim 37, wherein the determined ratio is (E6+E7)/L1.

39. The method of diagnosing risk of HPV 31-induced neoplasia of claim 37, wherein the determined ratio is (E6+E7)/(L1+L2).

40. The method of diagnosing risk of HPV 31-induced neoplasia of claim 37, wherein the determined ratio is (E2+E4+E6+E7)/(L1+L2).

41. The method of diagnosing risk of HPV 31-induced neoplasia of claim 37, wherein the determined ratio is (E6+E7)/E2.

42. A method of diagnosing the onset of HPV 31-induced neoplasia comprising the steps of:
quantifying a level of a group 1 HPV 31 mRNA from a sample collected from a patient infected with HPV31;
quantifying a level of a group 2 HPV 31 mRNA from a sample collected from said patient; and
determining a ratio of the quantified levels of the group 1 mRNA to group 2 mRNA,
wherein a ratio of greater than 2 is indicative of HPV 31-induced neoplastic onset.

43. A method of diagnosing the risk or onset of HPV 31-induced neoplasia comprising the steps of:
quantifying a level of a group 1 HPV 31 mRNA from a sample collected from a patient infected with HPV31;
quantifying a level of a group 3 HPV 31 mRNA from a sample collected from said patient; and
determining a ratio of the quantified levels of the group 1 mRNA to group 3 mRNA,
wherein a ratio of greater than 2 is indicative of high risk or onset of HPV 31-induced neoplastic onset.

44. A method of diagnosing the risk or onset of HPV 31-induced neoplasia comprising the steps of:
quantifying a level of a group 1 HPV 31 mRNA from a sample collected from a patient infected with HPV31;
quantifying a level of a group 2 HPV 31 mRNA from a sample collected from said patient;
quantifying a level of a group 3 HPV 31 mRNA from a sample collected from said patient; and
determining a ratio of the quantified level of the group 1 mRNA to the sum of the quantified levels of the group 2 mRNA and the group 3 mRNA,
wherein a ratio of greater than 2 is indicative of high risk or onset of HPV 31-induced neoplastic onset.

45. A method of diagnosing a stage of HPV 31-induced disease comprising the steps of:
quantifying a first level of one or more HPV 31 mRNA from a sample collected from a patient infected with HPV 31, wherein the one or more HPV 31 mRNA is selected from the group consisting of E6 mRNA and E7 mRNA;
quantifying a second level of one or more HPV 31 mRNA from a sample collected from said patient, wherein the one or more HPV 31 mRNA is selected from the group consisting of L1 mRNA, L2 mRNA, and E2 mRNA; and
determining a ratio of the quantified first and second levels of HPV 31 mRNA, wherein the ratio is selected from the group consisting of E6/L1, E6/L2, E6/E2, E6/(L1+L2), E6/(L1+E2), E6/(L2+E2), E6/(L1+L2+E2), E7/L1, E7/L2, E7/E2, E7/(L1+L2), E7/(L1+E2), E7/(L2+E2), E7/(L1+L2+E2), (E6+E7)/L1, (E6+E7)/L2, (E6+E7)/E2, (E6+E7)/(L1+L2), (E6+E7)/(L1+E2), (E6+E7)/(L2+E2), and (E6+E7)/(L1+L2+E2),
wherein any ratio of greater than 2 is indicative of early stage HPV 31-induced disease, thereby diagnosing a stage of HPV 31-induced disease in a patient infected with HPV.

46. The method of diagnosing a stage of HPV 31-induced disease of claim 45, wherein the determined ratio is E6/L1.

47. The method of diagnosing a stage of HPV 31-induced disease of claim 45, wherein the determined ratio is E6/L2.

48. The method of diagnosing a stage of HPV 31-induced disease of claim 45, wherein the determined ratio is E6/E2.

49. The method of diagnosing a stage of HPV 31-induced disease of claim 45, wherein the determined ratio is E6/(L1+L2).

50. The method of diagnosing a stage of HPV 31-induced disease of claim 45, wherein the determined ratio is E6/(L1+E2).

51. The method of diagnosing a stage of HPV 31-induced disease of claim 45, wherein the determined ratio is E6/(L2+E2).

52. The method of diagnosing a stage of HPV 31-induced disease of claim 45, wherein the determined ratio is E6/(L1+L2+E2).

53. The method of diagnosing a stage of HPV 31-induced disease of claim 45, wherein the determined ratio is E7/L1.

54. The method of diagnosing a stage of HPV 31-induced disease of claim 45, wherein the determined ratio is E7/L2.

55. The method of diagnosing a stage of HPV 31-induced disease of claim 45, wherein the determined ratio is E7/E2.

56. The method of diagnosing a stage of HPV 31-induced disease of claim 45, wherein the determined ratio is E7/(L1+L2).

57. The method of diagnosing a stage of HPV 31-induced disease of claim 45, wherein the determined ratio is E7/(L1+L2).

58. The method of diagnosing a stage of HPV 31-induced disease of claim 45, wherein the determined ratio is E7/(L2+E2).

59. The method of diagnosing a stage of HPV 31-induced disease of claim 45, wherein the determined ratio is E7/(L1+L2+E2).

60. The method of diagnosing a stage of HPV 31-induced disease of claim 45, wherein the determined ratio is (E6+E7)/L1.

61. The method of diagnosing a stage of HPV 31-induced disease of claim 45, wherein the determined ratio is (E6+E7)/L2.

62. The method of diagnosing a stage of HPV 31-induced disease of claim 45, wherein the determined ratio is (E6+E7)/E2.

63. The method of diagnosing a stage of HPV 31-induced disease of claim 45, wherein the determined ratio is (E6+E7)/(L1+L2).

64. The method of diagnosing a stage of HPV 31-induced disease of claim 45, wherein the determined ratio is (E6+E7)/(L1+E2).

65. The method of diagnosing a stage of HPV 31-induced disease of claim 45, wherein the determined ratio is (E6+E7)/(L2+E2).

66. The method of diagnosing a stage of HPV 31-induced disease of claim 45, wherein the determined ratio is (E6+E7)/(L1+L2+E2).

67. A method of diagnosing HPV 31-induced cancer comprising the steps of:
quantifying a first level of one or more HPV 31 mRNA from a sample collected from a patient infected with HPV, wherein the one or more HPV 31 mRNA is selected from the group consisting of E6 mRNA and E7 mRNA;

quantifying a second level of one or more HPV 31 mRNA from said patient, wherein the one or more HPV 31 mRNA is selected from the group consisting of E2 mRNA, E4 mRNA, L1 mRNA and L2 mRNA; and determining a ratio of the quantified first and second levels of HPV 31 mRNA, wherein the ratio is selected from the group consisting of (E6+E7)/L1, (E6+E7)/(L1+L2), and (E6+E7)/(E2+E4), wherein a ratio of greater than 4 is indicative of HPV 31-induced cancer.

68. The method of diagnosing HPV 31-induced cancer of claim 67, wherein the determined ratio is (E6+E7)/L1.

69. The method of diagnosing HPV 31-induced cancer of claim 67, wherein the determined ratio is (E6+E7)/(L1+L2).

70. The method of diagnosing HPV 31-induced cancer of claim 67, wherein the determined ratio is (E6+E7)/(E2+E4).

71. A method of diagnosing the risk or onset of HPV 31-induced cancer comprising the steps of:

quantifying a group 1 HPV 31 mRNA from a sample collected from a patient infected with HPV;

quantifying a group 2 HPV31 mRNA from a sample collected from a patient infected with HPV; and determining a ratio of group 1 mRNA level to group 2 mRNA level;

wherein any ratio of greater than 4 is indicative of high risk or onset of HPV 31-induced cancer.

72. A method of diagnosing the risk or onset of HPV 31-induced cancer comprising the steps of:

quantifying a group 1 HPV 31 mRNA from a sample collected from a patient infected with HPV;

quantifying a group 3 HPV 31 mRNA from a sample collected from a patient infected with HPV; and determining a ratio of group 1 mRNA level to group 3 mRNA level;

wherein any ratio of greater than 4 is indicative of high risk or onset of HPV 31-induced cancer.

73. A method of diagnosing risk of HPV 16-induced neoplasia comprising the steps of:

quantifying a first level of one or more HPV 16 mRNA from a sample collected from a patient infected with HPV, wherein the one or more HPV 16 mRNA is selected from the group consisting of E2 mRNA, E4 mRNA, E6 mRNA, and E7 mRNA;

quantifying a second level of one or more HPV 16 mRNA from a sample collected from said patient, wherein the one or more HPV 16 mRNA is selected from the group consisting of E2 mRNA, L1 mRNA, and L2 mRNA; and determining a ratio of the quantified first and second levels of HPV 16 mRNA, wherein the ratio is selected from the group consisting of (E6+E7)/L1, (E6+E7)/(L1+L2), (E2+E4+E6+E7)/(L1+L2), (E6+E7)/E2, wherein a ratio of greater than 2 is indicative of HPV 16-induced cell transformation and risk of neoplasia.

74. The method of diagnosing risk of HPV 16-induced neoplasia of claim 73, wherein the determined ratio is (E6+E7)/L1.

75. The method of diagnosing risk of HPV 16-induced neoplasia of claim 73, wherein the determined ratio is (E6+E7)/(L1+L2).

76. The method of diagnosing risk of HPV 16-induced neoplasia of claim 73, wherein the determined ratio is (E2+E4+E6+E7)/(L1+L2).

77. The method of diagnosing risk of HPV 16-induced neoplasia of claim 73, wherein the determined ratio is (E6+E7)/E2.

78. A method of diagnosing the onset of HPV 16-induced neoplasia comprising the steps of:

quantifying a level of a group 1 HPV 16 mRNA from a sample collected from a patient infected with HPV16;

quantifying a level of a group 2 HPV 16 mRNA from a sample collected from said patient; and determining a ratio of the quantified levels of the group 1 mRNA to group 2 mRNA, wherein a ratio of greater than 2 is indicative of HPV 16-induced neoplastic onset.

79. A method of diagnosing the risk or onset of HPV 16-induced neoplasia comprising the steps of:

quantifying a level of a group 1 HPV 16 mRNA from a sample collected from a patient infected with HPV16;

quantifying a level of a group 3 HPV 16 mRNA from a sample collected from said patient; and determining a ratio of the quantified levels of the group 1 mRNA to group 3 mRNA, wherein a ratio of greater than 2 is indicative of high risk or onset of HPV 16-induced neoplastic onset.

80. A method of diagnosing the risk or onset of HPV 16-induced neoplasia comprising the steps of:

quantifying a level of a group 1 HPV 16 mRNA from a sample collected from a patient infected with HPV16;

quantifying a level of a group 2 HPV 16 mRNA from a sample collected from said patient;

quantifying a level of a group 3 HPV 16 mRNA from a sample collected from said patient; and determining a ratio of the quantified level of the group 1 mRNA to the sum of the quantified levels of the group 2 mRNA and the group 3 mRNA, wherein a ratio of greater than 2 is indicative of high risk or onset of HPV 16-induced neoplastic onset.

81. A method of diagnosing a stage of HPV 16-induced disease comprising the steps of:

quantifying a first level of one or more HPV 16 mRNA from a sample collected from a patient infected with HPV 16, wherein the one or more HPV 16 mRNA is selected from the group consisting of E6 mRNA and E7 mRNA;

quantifying a second level of one or more HPV 16 mRNA from a sample collected from said patient, wherein the one or more mRNA is selected from the group consisting of L1 mRNA, L2 mRNA, and E2 mRNA; and determining a ratio of the quantified first and second levels of HPV 16 mRNA, wherein the ratio is selected from the group consisting of E6/L1, E6/L2, E6/E2, E6/(L1+L2), E6/(L1+E2), E6/(L2+E2), E6/(L1+L2+E2), E7/L1, E7/L2, E7/E2, E7/(L1+L2), E7/(L1+E2), E7/(L2+E2), E7/(L1+L2+E2), (E6+E7)/L1, (E6+E7)/L2, (E6+E7)/E2, (E6+E7)/(L1+L2), (E6+E7)/(L1+E2), (E6+E7)/(L2+E2), and (E6+E7)/(L1+L2+E2), wherein any ratio of greater than 2 is indicative of early stage HPV 16-induced disease, thereby diagnosing a stage of HPV 16-induced disease in a patient infected with HPV.

82. The method of diagnosing a stage of HPV 16-induced disease of claim 81, wherein the determined ratio is E6/L1.

83. The method of diagnosing a stage of HPV 16-induced disease of claim 81, wherein the determined ratio is E6/L2.

84. The method of diagnosing a stage of HPV 16-induced disease of claim 81, wherein the determined ratio is E6/E2.

85. The method of diagnosing a stage of HPV 16-induced disease of claim 81, wherein the determined ratio is E6/(L1+L2).

86. The method of diagnosing a stage of HPV 16-induced disease of claim 81, wherein the determined ratio is E6/(L1+E2).

87. The method of diagnosing a stage of HPV 16-induced disease of claim 81, wherein the determined ratio is E6/(L2+E2).

88. The method of diagnosing a stage of HPV 16-induced disease of claim 81, wherein the determined ratio is E6/(L1+L2+E2).

89. The method of diagnosing a stage of HPV 16-induced disease of claim 81, wherein the determined ratio is E7/L1.

90. The method of diagnosing a stage of HPV 16-induced disease of claim 81, wherein the determined ratio is E7/L2.

91. The method of diagnosing a stage of HPV 16-induced disease of claim 81, wherein the determined ratio is E7/E2.

92. The method of diagnosing a stage of HPV 16-induced disease of claim 81, wherein the determined ratio is E7/(L1+L2).

93. The method of diagnosing a stage of HPV 16-induced disease of claim 81, wherein the determined ratio is E7/(L1+E2).

94. The method of diagnosing a stage of HPV 16-induced disease of claim 81, wherein the determined ratio is E7/(L2+E2).

95. The method of diagnosing a stage of HPV 16-induced disease of claim 81, wherein the determined ratio is E7/(L1+L2+E2).

96. The method of diagnosing a stage of HPV 16-induced disease of claim 81, wherein the determined ratio is (E6+E7)/L1.

97. The method of diagnosing a stage of HPV 16-induced disease of claim 81, wherein the determined ratio is (E6+E7)/L2.

98. The method of diagnosing a stage of HPV 16-induced disease of claim 81, wherein the determined ratio is (E6+E7)/E2.

99. The method of diagnosing a stage of HPV 16-induced disease of claim 81, wherein the determined ratio is (E6+E7)/(L1+L2).

100. The method of diagnosing a stage of HPV 16-induced disease of claim 81, wherein the determined ratio is (E6+E7)/(L1+E2).

101. The method of diagnosing a stage of HPV 16-induced disease of claim 81, wherein the determined ratio is (E6+E7)/(L2+E2).

102. The method of diagnosing a stage of HPV 16-induced disease of claim 81, wherein the determined ratio is (E6+E7)/(L1+L2+E2).

103. A method of diagnosing HPV 16-induced cancer comprising the steps of:
quantifying a first level of one or more HPV 16 mRNAs from a sample collected from a patient infected with HPV, wherein the one or more HPV 16 mRNA is selected from the group consisting of E6 mRNA and E7 mRNA;
quantifying a second level of one or more HPV 16 mRNA from said patient, wherein the one or more mRNA is selected from the group consisting of E2 mRNA, E4 mRNA, L1 mRNA and L2 mRNA; and
determining a ratio of the quantified first and second levels of HPV 16 mRNA, wherein the ratio is selected from the group consisting of (E6+E7)/L1, (E6+E7)/(L1+L2), and (E6+E7)/(E2+E4),
wherein a ratio of greater than 4 is indicative of HPV 16-induced cancer.

104. The method of diagnosing HPV 16-induced cancer of claim 103, wherein the determined ratio is (E6+E7)/L1.

105. The method of diagnosing HPV 16-induced cancer of claim 103, wherein the determined ratio is (E6+E7)/(L1+L2).

106. The method of diagnosing HPV 16-induced cancer of claim 103, wherein the determined ratio is (E6+E7)/(E2+E4).

107. A method of diagnosing the risk or onset of HPV 16-induced cancer comprising the steps of:
quantifying a group 1 HPV 16 mRNA from a sample collected from a patient infected with HPV;
quantifying a group 2 HPV 16 mRNA from a sample collected from a patient infected with HPV; and
determining a ratio of group 1 mRNA level to group 2 mRNA level;
wherein any ratio of greater than 4 is indicative of high risk or onset of HPV 16-induced cancer.

108. A method of diagnosing the risk or onset of HPV 16-induced cancer comprising the steps of:
quantifying a group 1 HPV 16 mRNA from a sample collected from a patient infected with HPV;
quantifying a group 3 HPV 16 mRNA from a sample collected from a patient infected with HPV; and
determining a ratio of group 1 mRNA level to group 3 mRNA level;
wherein any ratio of greater than 4 is indicative of high risk or onset of HPV 16-induced cancer.

\* \* \* \* \*